US009932372B2

(12) United States Patent
Wang et al.

(10) Patent No.: US 9,932,372 B2
(45) Date of Patent: Apr. 3, 2018

(54) DESIGNER PEPTIDE-BASED PCV2 VACCINE

(75) Inventors: Chang Yi Wang, Cold Spring Harbor, NY (US); Wen-Jiun Peng, Taoyuan (TW)

(73) Assignee: UNITED BIOMEDICAL, INC., Hauppauge, NY (US)

( * ) Notice: Subject to any disclaimer, the term of this patent is extended or adjusted under 35 U.S.C. 154(b) by 215 days.

(21) Appl. No.: 13/808,974

(22) PCT Filed: Jul. 8, 2010

(86) PCT No.: PCT/US2010/041406

§ 371 (c)(1),
(2), (4) Date: May 21, 2013

(87) PCT Pub. No.: WO2012/005732

PCT Pub. Date: Jan. 12, 2012

(65) Prior Publication Data

US 2013/0236487 A1 Sep. 12, 2013

(51) Int. Cl.

*C07K 14/01* (2006.01)
*A61K 39/12* (2006.01)
*G01N 33/68* (2006.01)
*A61K 39/00* (2006.01)

(52) U.S. Cl.

CPC .............. *C07K 14/01* (2013.01); *A61K 39/12* (2013.01); *G01N 33/6878* (2013.01); *A61K 2039/552* (2013.01); *A61K 2039/55566* (2013.01); *A61K 2039/6031* (2013.01); *C12N 2710/24111* (2013.01); *C12N 2710/24143* (2013.01); *C12N 2770/32011* (2013.01); *C12N 2770/32034* (2013.01)

(58) Field of Classification Search

None

See application file for complete search history.

(56) References Cited

U.S. PATENT DOCUMENTS

| | | | |
|---|---|---|---|
| 5,229,490 A | 7/1993 | Tam | |
| 6,025,468 A | 2/2000 | Wang | |
| 6,107,021 A | 8/2000 | Wang et al. | |
| 6,713,301 B1 * | 3/2004 | Wang | 435/328 |
| 6,906,169 B2 | 6/2005 | Wang | |
| 7,371,395 B2 * | 5/2008 | Parisot et al. | 424/283.1 |
| 2003/0165478 A1 * | 9/2003 | Sokoll | 424/93.21 |
| 2004/0009897 A1 | 1/2004 | Sokoll | |
| 2006/0029615 A1 | 2/2006 | Ren et al. | |
| 2008/0248061 A1 | 10/2008 | Roerink et al. | |
| 2008/0267995 A1 | 10/2008 | Roof et al. | |
| 2009/0010954 A1 | 1/2009 | Fachinger et al. | |
| 2009/0017064 A1 | 1/2009 | Wu et al. | |
| 2009/0022749 A1 | 1/2009 | Eichmeyer et al. | |
| 2009/0162398 A1 | 6/2009 | Wu | |
| 2010/0129397 A1 | 5/2010 | Fachinger et al. | |
| 2010/0233196 A1 * | 9/2010 | Dupuis et al. | 424/184.1 |
| 2013/0236487 A1 * | 9/2013 | Wang et al. | 424/186.1 |

FOREIGN PATENT DOCUMENTS

| | | | |
|---|---|---|---|
| JP | H11-504635 | | 4/1999 |
| JP | 2002-518462 | | 6/2002 |
| JP | 2011-511754 | | 4/2011 |
| KR | 10-2006-0088908 | | 8/2006 |
| KR | 10-2009-0088938 | | 8/2009 |
| WO | 96/34888 | | 7/1996 |
| WO | 1999-029717 | | 6/1999 |
| WO | 99/66957 | | 12/1999 |
| WO | WO 2005/092069 | * | 10/2005 |
| WO | WO 2006/072065 | * | 7/2006 |
| WO | 2008-076915 | | 6/2008 |
| WO | WO 2009/000459 | * | 12/2008 |

OTHER PUBLICATIONS

Gamage et al. (Vaccine. 2009; 27: 6595-6604).*
Sequence alignment of SEQ ID No. 1 with Geneseq access No. AED07735, submitted on Dec. 1, 2005 by Meng et al. in WO 2005/092069.*
Sequence alignment of SEQ ID No. 1 with UniProt access No. B8Y5Y9_PCV2, submitted on Mar. 3, 2009 by Liu et al. in Virus Research. 2007; 127: 95-99.*
Liu et al. (Virus Research. 2007; 127: 95-99).*
Sequence alignment of SEQ ID No. 9 with Geneseq access No. AWF75404, submitted by Wu et al. on Apr. 2, 2009 in USPgPub 2009/017064.*
Sequence alignment of SEQ ID No. 10 with Geneseq access No. AWF75404, submitted by Wu et al. on Apr. 2, 2009 in USPgPub 2009/017064.*
Sequence alignment of SEQ ID No. 11 with UniProt database access No. D3GGZ7_PCV2, submitted by Kappe et al. on Mar. 23, 2010 in Berl. Munch. Tierarztl. Wochenschr. 2010; 123: 131-141.*
Sequence alignment of SEQ ID No. 12 with UniProt access No. C9EJT9_PCV2, submitted by Cortey et al. Nov. 3, 2009 in (Veterinary Journal. 2011; 187: 363-368).*
Sequence alignment of instant SEQ ID No. 7: with Geneseq access No. AAW51458, submitted by Larson et al. in WO 98/11126 on Sep. 1998.*
Sequence alignment of instant SEQ ID No. 3 with Geneseq access No. AAY31794, submitted by Poet et al. in WO 99/45956 on Sep. 1999.*
The sequence alignment of instant SEQ ID No. 4 with Geneseq database access No. AAY24929, submitted by Wang et al. in WO 99/29717 on Jun. 1999.*
Sequence alignment of SEQ ID No. 5 with Geneseq access No. AAY24930, submitted by Wang et al. in WO 99/29717 on Jun. 1999.*
Lekcharoensuk et al. (Journal of Virology. 2004; 78 (15): 8135-8145).*

(Continued)

*Primary Examiner* — Shanon A. Foley
(74) *Attorney, Agent, or Firm* — Locke Lord, LLP

(57) ABSTRACT

Porcine circovirus (PCV2) vaccine compositions comprising a peptide antigen derived from a PCV2 capsid protein are described. In various embodiments, the peptide antigen contains amino acids of the capsid protein from about amino acid 47 to about amino acid 202. In some embodiments, the peptide antigen is optionally linked to an artificial T helper epitope and/or mixed with T helper epitopes derived from the ORF1 and ORF3 proteins of PCV2. Methods of using PCV2 vaccine compositions are also described. In various embodiments, a vaccine composition is used in animals for the prevention of PCV2 infection. In other embodiments, a PCV2 vaccine composition is used as an antigen for diagnosing PCV2 infection.

20 Claims, 3 Drawing Sheets

(56) References Cited

OTHER PUBLICATIONS

Allan, GM, et al. "Porcine circoviruses: A review." J Vet Diagn Invest, 12:3-14, (2000).

Blanchard, P, et al. "Protection of swine against post-weaning multisystemic wasting syndrome (PMWS) by porcine circovirus type 2 (PCV2) proteins." Vaccine; 21:4565-4575, (2003).

Chen, C-M., et al. "Effects of PCV2 infection in a transgenic SPF pig farm in Taiwan." 13th AAAP Anim. Sci. Congr. Sep. 22-26, Hanoi, Vietnam. Proceedings, p. 420, (2008).

Cheung, AK. "Transcriptional analysis of porcine circovirus type 2." Virology, 305:168-180, (2003).

Fuerst, TR, et al. "Eukaryotic transient-expression system based on recombinant vaccinia virus that synthesizes bacteriophage T7 RNA polymerase." Proc. Natl. Acad. Sci. USA; 83:8122-8126, (1986).

GenBank Accession No. AAN62766, "Putative Capsid Protein (Porcine circovirus-2)", Nov. 6, 2002.

Harlow, E, et al. "Antibodies: A Laboratory Manual." Chapter 14 Immunoassays, pp. 555-612. Cold Spring Harbor Laboratory, Cold Spring Harbor, NY, (1988).

Liu, J, et al. "The ORF3 protein of porcine circovirus type 2 is involved in viral pathogenesis in vivo." J Virol; 80:5065-5073, (2006).

Mahe, D, et al. "Differential recognition of ORF2 protein from type 1 and type 2 porcine circoviruses and identification of immunorelevant epitopes." J Gen Virol; 81:1815-1824, (2000).

Mankertz, A, et al. "Molecular biology of Porcine circovirus: Analyses of gene expression and viral replication." Vet Microbiol; 98:81-88, (2004).

McIntosh, KA, et al. "Quantitative polymerase chain reaction for Porcine circovirus-2 in swine feces in a Porcine circovirus disease-affected commercial herd and a nonaffected commercial herd." Can Vet J; 49:1189-1194, (2008).

Meehan, BM, et al. "Characterization of novel circovirus DNAs associated with wasting syndromes in pigs." J Gen Virol; 79:2171-2179, (1998).

Meloen, RH, et al. "The use of peptides to reconstruct conformational determinants; a brief review." Ann Biol Clin; 49:231-242, (1991).

Nawagitgul, P, et al. "Open reading frame 2 of porcine circovirus type 2 encodes a major capsid protein." J Gen Virol; 81:2281-2287, (2000).

Partidos, CD, et al. "Immune responses in mice following immunization with chimeric peptides representing B and T cell epitopes of measles virus protein." J Gen Virol; 72:1293-1299, (1991).

Saiz, JC, et al. "Heterotypic lymphoproliferative response in pigs vaccinated with foot-and-mouth disease virus. Involvement of isolated capsid proteins." J Gen Virol; 73:2601-2607, (1992).

Stenvenson, LS, et al. "T lymphocyte epitope mapping of porcine circovirus type 2." Viral Immunology; 20:389-397, (2007).

Walker, IW, et al. "Development and application of a competitive enzyme-linked immunosorbent assay for the detection of serum antibodies to porcine circovirus type 2." J Vet Diagn Invest; 12:400-405, (2000).

Wang, CY, et al. "Site-specific peptide vaccines for immunotherapy and immunization against chronic diseases, cancer, infectious diseases, and for veterinary applications." Vaccine; 23:2049-2056, (2005).

Wang, CY, et al. "Synthetic AIDS vaccine by targeting HIV receptor." Vaccine; 21:89-97, (2002).

International Search Report issued in corresponding international application PCT/US2010/041406, dated Jan. 12, 2011.

International Preliminary Report on Patentability issued in corresponding international application PCT/US2010/041406, dated Jan. 8, 2013.

Search Report, issued in corresponding Taiwanese Patent Application No. 100123478 (now TW Patent I508740), search completed Aug. 14, 2013, search report issued Aug. 22, 2013.

Search Report, issued in corresponding European Patent Application No. 10854531.0, search completed Oct. 15, 2015, search report issued Oct. 27, 2015.

Gillogly, ME, et al., "Ii-Key/HER-2/neu MHC class-II antigenic epitope vaccine peptide for breast cancer", Cancer Immunol. Immunother., 53(6):490-496 (2004).

* cited by examiner

DESIGNER PEPTIDE-BASED PCV2 VACCINE

FIELD OF THE INVENTION

This disclosure relates to a peptide-based vaccine against porcine circovirus type 2 (PCV2) and a method for the manufacture of such a vaccine for protecting piglets against PCV2 infection even in the face of short-lived but relatively high titers of maternally derived antibodies against PCV2.

Vaccine formulations according to various embodiments of the invention contain a peptide derived from open reading frame 2 (ORF2)-encoded capsid protein, which is optionally linked to an artificial T helper epitope to enhance its B cell immunogenicity, which can be optionally supplemented with a mixture of peptides derived from PCV2 ORF1 and ORF3 containing clusters of PCV2 T helper epitopes, prepared in a veterinarily acceptable delivery system as vaccine formulations.

BACKGROUND OF THE INVENTION

Porcine circovirus (PCV) was identified in 1974 as a picornavirus-like contaminant of a pig kidney tissue culture cell line (PK15) (1). In 1998, an antigenically and genetically distinct PCV was isolated from pig tissue and named Porcine circovirus type 2 (PCV2); PCV2 is associated with clinical disease in pigs (2).

Postweaning multisystemic wasting syndrome (PMWS), an emerging and economically important disease in swine, is caused by PCV2. However, evidence suggests that manifestation of the signs of PMWS requires co-infection with a pathogen such as Porcine parvovirus (PPV) or a similar immune stimulant, stress, or cofactor. This syndrome debilitates swine 7 to 15 weeks of age, with wasting, respiratory distress, enlarged lymph nodes, diarrhea, pallor, and jaundice. Also, gross and histologic lesions can affect multiple organ systems and are associated with interstitial pneumonia, lymphadenopathy, hepatitis, nephritis, myocarditis, enteritis, dermatitis, and pancreatitis (1,3).

Antibodies specific for PCV2 have been retrospectively detected in swine serum dating back to 1973 (4). Diagnosis of PMWS relies on the detection of either PCV2-specific nucleic acid or antigen associated with lesions in affected tissues. The virus has been isolated from heart, lung, liver, kidney, spleen, salivary gland, lymph node, thyroid, thymus, gastrointestinal tract, feces, pancreas, testes, and brain (1,5).

The primary route of transmission is unknown, but evidence suggests that PCV2 can be transmitted both horizontally and vertically. It has been detected in ocular, nasal, and fecal samples from naturally infected swine. Isolation of PCV2 from aborted pig fetal tissue suggests vertical transmission. Detection of PCV2 nucleic acid in the semen of naturally and experimentally infected boars suggests transmission from boars to PCV2-naïve gilts and their litters (5).

Porcine circovirus type 2 (PCV2) is a small nonenveloped virus with a circular single-stranded DNA (ssDNA) genome. The genome comprises six open reading frames (ORFs) encoding putative proteins (2) with four ORFs sharing significant homology with analogous ORFs from the non-pathogenic porcine circovirus type 1 (PCV1) (6). Only proteins encoded by ORF1, ORF2, and ORF3 have been detected in PCV2-infected cells. ORF1 encodes the 312 amino acid replicase protein and also gives rise to a 168 amino acid spliced variant, both of which are essential for PCV2 replication (7). The structural capsid protein is encoded by ORF2 (8); and ORF3 encodes a highly conserved protein that is not essential for replication but plays an important role in PCV2-induced apoptosis and pathogenicity (9).

Only the surface-exposed PCV2 ORF2-encoded capsid protein is capable of eliciting a protective antibody response by the B cells of the host's immune system (10). Consistent with that observation, PEPSCAN mapping studies localized clusters of immunodominant B cell epitopes with specificity to PCV2 primarily to areas on the PCV2 capsid protein, at residues 65-87, 113-139, 169-183, and 193-207 (11). In addition to B cell epitopes, immunodominant T cell epitopes, including T helper cell epitopes, are another important factor affecting the antigenicity of a virus. T helper cell epitopes elicit protective T helper cell (Th) responses that signal B cells to produce antibody. In contrast to the localization of B cell epitopes to the capsid protein (11), T cell epitope mapping of PCV2 with 20 mer peptides and lymphocyte proliferation assays indicated that immunodominant Th responses are most consistently localized to epitopes on the nonstructural proteins of ORF1 and ORF3, whereas no linear Th epitopes encoded by ORF2 displayed immunodominance (12).

Presentation of Th determinants to the immune system by a synthetic peptide is a critical factor controlling the immunogenicity of a synthetic peptide. Th epitopes that are immunodominant and promiscuous are highly and broadly reactive in populations of divergent MHC types (13). Thus, the scarcity of immunodominant Th sites on the capsid protein helps to account for the limited immunogenicity of subunit capsid vaccines for PCV2. The immunogenicity of a peptide subunit immunogen can be strengthened by covalent linkage of a targeted B cell epitope to selected foreign promiscuous Th sites, including a promiscuous Th epitope whose genetic responsiveness is enlarged through combinatorial chemistry (14, 15, 16). In addition, the immunopotency of a vaccine in swine and protection of swine from viral infection afforded by the vaccine can be influenced by multiple Th epitopes of the virus, and these can be cross-protective in combination with B cell epitopes from different proteins (17).

There is a need for a low cost highly specific vaccine that protects piglets against PCV2-related diseases such as PMWS. Conventional vaccines for pigs are based on inactivated whole PCV2 virus. However, PCV2 does not replicate to high titers in cell culture, making conventional vaccines costly and of low potency. Alternative vaccines are based on recombinant PCV2 ORF2 antigens. PCV2 ORF2 capsid subunits have been expressed in various expression systems including the baculovirus expression system in insect cells (3,10). In most applications, insect cells which produce the recombinant PCV2 capsid proteins are lysed and formulated into vaccines that are used to vaccinate piglets. Such recombinant antigens frequently contain host cell and vector-encoded antigens thus rendering the vaccine nonspecific and can cause severe untoward immune responses including anaphylaxis.

Another problem with inactivated virus PCV2 vaccines, and with subunit capsid vaccines either as recombinant virus lysates or as purified protein, is their relatively low potencies when used in normal field piglets. They are commonly tested in specific pathogen-free (SPF) piglets or cesarean-derived colostrum deprived (CDCD) piglets because those in the field often have maternally-derived antibodies (MDA). These maternal antibodies, while typically of titers too low and of too short duration to provide protection, are still high enough to interfere with vaccination. This interference by MDA can be partially overcome by administration of a high dose of recombinant ORF2 capsid antigen (18). A recombinant full-length ORF2 antigen was secreted into the medium by the baculovirus expression system disclosed in US2009/0022749A1 (19). This system partially alleviates problems of low yield and purity; however, this system and the other biological expression systems suffer from the inherently limited immunogenicity of full-length PVC2 antigen preparations, and they endure costly problems stemming from non-reproducibility, low yields, and complicated quality control protocols. Thus, it is desirable to develop a PCV2 vaccine through a process of rational design, through which immunogenic peptides are designed and synthesized. Such peptide-based vaccines can be designed to contain capsid-specific B cell epitopes, potent foreign Th epitopes and PCV2 Th epitopes derived from other PCV2 proteins, and used in combination as the key ingredient of a vaccine formulation, to elicit anti-capsid antibody responses that precisely confront PCV2 infection in piglets.

The rational design of immunogenic peptides for a virus vaccine begins with the identification of immunodominant epitopes by epitope mapping. Epitope mapping employs a series of overlapping peptides corresponding to regions of interest on a targeted virus protein to identify sites which participate as immunogenic determinants in interactions with the immune system. Most commonly, epitope mapping employs peptides of relatively short length to precisely detect linear determinants. A fast method of epitope mapping known as "PEPSCAN" is based on the simultaneous synthesis of hundreds of overlapping peptides, coupled to solid supports. The coupled peptides are tested for their abilities to bind antibodies or to stimulate T cell proliferation. This approach is effective in localizing linear B and T cell determinants; however, the immunodominant B cell epitopes of a targeted virus or protein that are essential for vaccine development are usually long high affinity discontinuous epitopes that are difficult to define by the PEPSCAN method (20).

There is a need for the identification of immunogenic PCV2 peptides bearing long discontinuous epitopes which can be chemically synthesized in milligram to kilogram quantities by controlled and reproducible solid-phase peptide synthesis. This controlled commercial scale process for the synthesis of PCV2 capsid immunogens, together with the straightforward means to characterize such peptide products, would provide a framework for the low cost commercial scale manufacture and quality control of PCV vaccine formulations (21).

REFERENCES

1. Allan G M, and Ellis J A. Porcine circoviruses: A review. J Vet Diagn Invest 2000; 12:3-14.
2. Meehan B M, McNeilly F, Todd D, Kennedy S, Jewhurst V A, Ellis J A, Hassard L E, Clark E G, Haines D M, and Allan G M. Characterization of novel circovirus DNAs associated with wasting syndromes in pigs. J Gen Virol 1998; 79:2171-2179.
3. Roof M, Hayes P, Eichmeyer M, Nitzel G, and Schaeffer M. Use of a PCV2 immunogenic composition for lessening clinical symptoms in pigs. US 2008/0267995A1.
4. Walker I W, Konoby C A, Jewhurst V A, McNair I, McNeilly F, Meehan B M, Cottrell T S, Ellis J A, and Allan G M: Development and application of a competitive enzyme-linked immunosorbent assay for the detection of serum antibodies to porcine circovirus type 2. J Vet Diagn Invest 2000; 12:400-405.
5. McIntosh K A, Harding J C S, Parker S, Krakowka S, Allan G, and Ellis J A. Quantitative polymerase chain reaction for Porcine circovirus-2 in swine feces in a Porcine circovirus disease-affected commercial herd and a nonaffected commercial herd. Can Vet J 2008; 49:1189-1194.
6. Mankertz A, Caliskan R, Hattermann K, Hillenbrand B, Kurzendoerfer P, Mueller B, Schmitt C, Steinfeldt T, and Finsterbusch T. Molecular biology of Porcine circovirus: Analyses of gene expression and viral replication. Vet Microbiol 2004; 98:81-88.
7. Cheung A K. Transcriptional analysis of porcine circovirus type 2. Virology 2003; 305:168-180.
8. Nawagitgul P, Morozov I, Bolin S R, Harms P A, Sorden S D, and Paul P S. Open reading frame 2 of porcine circovirus type 2 encodes a major capsid protein. J Gen Virol 2000; 81:2281-2287.
9. Liu J, Chen I, Du Q, Chua H, and Kwang J. The ORFS protein of porcine circovirus type 2 is involved in viral pathogenesis in vivo. J Virol 2006; 80:5065-5073.
10. Blanchard P, Mahé D, Cariolet R, Keranflec'h A, Baudouard M A, Cordioli P, Albina E, and Jestin A. Protection of swine against post-weaning multisystemic wasting syndrome (PMWS) by porcine circovirus type 2 (PCV2) proteins. Vaccine 2003; 21:4565-4575.
11. Mahé D, Blanchard P, Truong C, Arnauld C, Le Cann P, Cariolet R, Madec F, Albina E, and Jestin A. Differential recognition of ORF2 protein from type 1 and type 2 porcine circoviruses and identification of immunorelevant epitopes. J Gen Virol 2000; 81:1815-1824.
12. Stevenson L S, Gilpin D F, Douglas A, McNeilly F, McNair I, Adair B M, and Allan G M. T lymphocyte epitope mapping of porcine circovirus type 2. Viral Immunology, 2007; 20:389-397.
13. Partidos C D, Stanley C M, and Steward M W Immune responses in mice following immunization with chimeric peptides representing B and T cell epitopes of measles virus protein. J Gen Virol 1991; 72:1293-1299.
14. Wang C Y. Artificial T helper cell epitopes as immune stimulators for synthetic peptide immunogens including immunogenic LHRH peptides. U.S. Pat. No. 6,025,468.
15. Wang C Y. Artificial T helper cell epitopes as immune stimulators for synthetic peptide immunogens. U.S. Pat. No. 6,713,301.
16. Wang C Y Immunogenic peptide composition comprising measles virus F protein T helper cell epitope (MVFThL-16) and N-terminus of β-amyloid peptide. U.S. Pat. No. 6,906,169.
17. Sáiz J C, Rodriguez A, Gonzalez M, Alonso F, and Sobrino F. Heterotypic lymphoproliferative response in pigs vaccinated with foot-and-mouth disease virus. Involvement of isolated capsid proteins. J Gen Virol 1992; 73:2601-2607.
18. Roerink F, and van Woensel P. PCV2 Vaccine. US2008/0248061A1.
19. Eichmeyer M, Nitzel G, and Schaeffer M. PCV2 immunogenic compositions and methods of producing such compositions. US2009/0022749A1.
20. Meloen R H, Amerongen A V, Hage-Van Noort M, Langedijk J P M, Posthumus W P A, Puyk W C, Plasman H, Lenstra J A, Langeveld J P M. The use of peptides to reconstruct conformational determinants; a brief review. Ann Biol Clin 1991; 49:231-242.
21. Wang C Y and Walfield A M. Site-specific peptide vaccines for immunotherapy and immunization against chronic diseases, cancer, infectious diseases, and for veterinary applications. Vaccine 2005; 23:2049-2056.

22. Fuerst T R, Niles E G, Studier F W, and Moss B. Eukaryotic transient-expression system based on recombinant vaccinia virus that synthesizes bacteriophage T7 RNA polymerase. Proc. Natl. Acad. Sci. USA 1986; 83:8122-8126.
23. Chen C-M., Liu H-T, Tu C-F. Effects of PCV2 infection in a transgenic SPF pig farm in Taiwan. 13th AAAP Anim Sci. Congr. Sep. 22-26, 2008 Hanoi, Vietnam. Proceedings, p. 420.
24. Wang C Y, Shen M, Tam G, Fang X D, Ye J, Shen F, Walfield A M, Wang J J G, Li M L, Li X M, Salas M, Shearer M H, Kennedy R C, and Hanson C V. Synthetic AIDS vaccine by targeting HIV receptor. Vaccine 2002; 21:89-97.
25. Wang C Y, Shen M. Synthetic peptide vaccines for foot-and-mouth disease. U.S. Pat. No. 6,107,021.
26. Harlow E and Lane D. Antibodies: A Laboratory Manual. Chapter 14 Immunoassays, pp 555-612. Cold Spring Harbor Laboratory, Cold Spring Harbor, N.Y. 1988.
27. Sokoll K K. Stabilized synthetic immunogen delivery system. United States Patent Application Publication No. US 2003/0165478.

BRIEF DESCRIPTION OF THE INVENTION

This disclosure relates to porcine circovirus type 2 (PCV2) vaccines comprising a peptide or peptide composition wherein the peptide or peptide composition is optimized by screening overlapping short and long PCV2 capsid peptides for serological reactivities. Such empirical findings detected a cluster of immunodominant B cell epitopes within the PCV2 capsid protein as exemplified by GenBank Accession Number AAN62766. Specifically, the cluster of immunodominant B cell epitopes was found on a 154 amino acid long peptide of the PCV2 capsid protein (peptide Cap1, SEQ ID NO:1, also shown in Table 1). This peptide was incorporated into a peptide-based vaccine as a key immunogen to elicit protective antibody and cell-mediated immune responses against PCV2 infection and was augmented by additional foreign and PCV2-derived T cell epitopes. Said peptide immunogens are useful for the formulation of vaccines against PCV2.

Various embodiments of the invention relate to methods for the manufacture of such peptide, peptide composition and pharmaceutical formulation as vaccines for elicitation of immune responses that can protect piglets against PCV2 infection, and for the manufacture of diagnostic kits for detection of PCV2 infection.

Various embodiments of the invention are directed to vaccine formulations which contain the designed PCV2 Cap1 peptide (SEQ ID NO: 1), and homologues and analogues thereof, derived from ORF2 capsid protein. The PCV2 Cap1 peptide in these formulations is preferentially, but optionally, linked to an artificial combinatorial T helper epitope (SEQ ID NO: 2, also shown in Table 1) to enhance its B cell immunogenicity. The PCV2 Cap1 peptide can also be optionally mixed with a mixture of PCV2 ORF1 (SEQ ID NOS: 3 and 4) and ORF3 (SEQ ID NO: 5) peptides containing clusters of PCV2 Th epitopes (also shown in Table 1). Such peptide-based PCV2 vaccine formulations elicit PCV2-specific antibody responses that protect against PCV2 infection in piglets, including those that may have maternally derived antibodies (MDA) that may interfere with vaccination. Such designed peptide-based vaccines contain peptide compositions as immunogens that can be chemically synthesized at milligram to kilogram scales for industrial application, and be readily quality controlled.

Also provided by various embodiments of the invention are adjuvants and/or delivery vehicles and other ingredients routinely incorporated with vaccine formulations.

BRIEF DESCRIPTIONS OF THE FIGURES

FIG. 1A is an illustration showing the mechanism for detecting antibodies to PCV2 capsid protein bound to capsid inside the nucleus of co-transfected HTK cell line cells by immunofluorescence according to an embodiment of the invention. The illustration shows HTK cells infected with T7 polymerase recombinant vaccinia virus (T7/vac) (22) and co-transfected with the pCR-orf2 plasmid by Lipofectamine™ (Invitrogen). The recombinant capsid protein transports to the nucleus after it is translated (23). Anti-capsid antibodies, according to one embodiment of the invention, become bound to the nucleus of the transfected HTK host cells where they are detected by the immunofluorescence of a labeled secondary antibody. This method affords for detection of antibodies to authentic PCV2 capsid protein with high specificity through transient eukaryotic expression in the HTK cells of full length PCV2 capsid protein, mediated by the prokaryotic T7 promotor.

DETAILED DESCRIPTION OF THE INVENTION

Figure 1A:
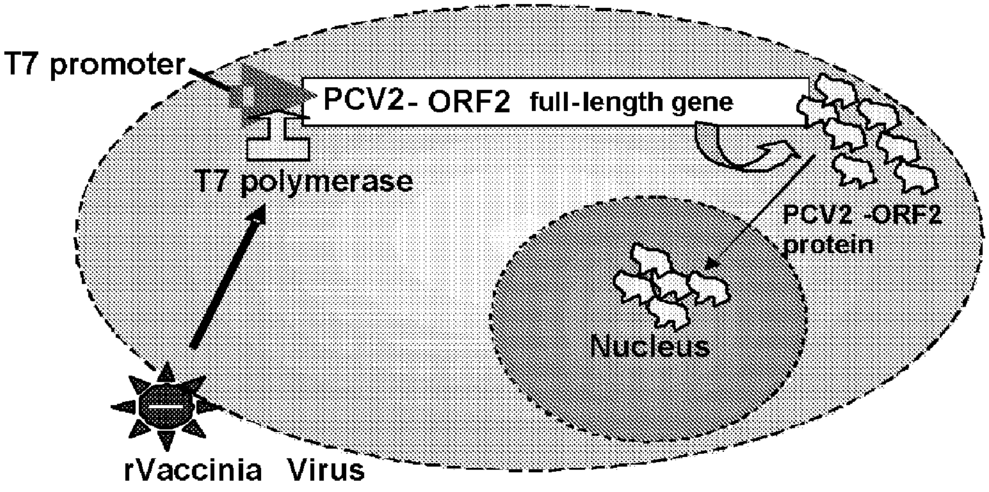
FIG. 1B is an Immunofluorescence Assay (IFA) carried out according to the mechanism described in FIG. 1A. Co-transfected HTK cell line cells with antibodies to PCV2 capsid protein bound to capsid inside the nucleus are detected.

Peptide antigens can detect immunological responses and certain peptide antigens may also stimulate immunological responses. Many peptide antigens can be used for the sensitive and specific detection of immune responses but most often they do not by themselves act as immunogens. Peptide immunogens are a special class of peptide antigens that can be used to stimulate immune responses as well as detect them. According to one embodiment of the invention, the peptide antigens in the PCV2 vaccine are peptide immunogens that have both B cell and T helper cell (Th) epitopes that together act to stimulate the generation of protective immune responses, in addition to being capable of detecting immune responses to PCV2 infection.

One method for identification of B cell epitopes relies on a set of nested and overlapping peptides of multiple lengths, typically ranging from 20 to 60 residues or longer in length. These longer peptides are synthesized by a laborious series of independent solid-phase peptide syntheses, rather than by the rapid and simultaneous PEPSCAN syntheses. The resulting sets of nested and overlapping peptides can then be used in antibody binding studies and experimental immunizations to identify long peptides which best present immunodominant determinants, including discontinuous conformational B cell epitopes. This method has been utilized for the selection of a non-linear determinant on CD4 that is used in a vaccine to block binding by the gp120 glycoprotein of HIV (24), and for the design of a potent peptide antigen from the G-H loop domain of the VP1 protein of foot-and-mouth disease virus (25).

One embodiment of the invention provides for PCV2 ORF2-encoded capsid peptides that comprise a 154 mer amino acid sequence (SEQ ID NO: 1, also shown in Table 1) having a cluster of B cell epitopes for optimal antibody recognition. These antigenic peptides were empirically identified and optimized using serum samples from PCV2-infected piglets and an ELISA immunoassay format. Any immunoassay format that can be adapted to an antibody capture phase comprising peptide antigens, e.g., ELISA, can be used to detect and quantitate antibodies that bind to a particular fragment of a PCV2 capsid protein in a blood, serum, or plasma sample from a PCV2-infected pig.

In a specific embodiment, an optimized PCV2 antigenic peptide of about 154 amino acids (SEQ ID NO: 1), which corresponds to amino acid residues 47-202 of a full-length PCV2 protein, presents immunogenic and antigenic sites of PCV2 capsid that are most useful both for the generation of protective antibodies by vaccination and for the detection of antibodies for diagnosis by ELISA. This highly antigenic and immunogenic capsid peptide was identified from among a collection of more than 50 overlapping peptides with lengths from 20 to 170 residues that were designed, synthesized and tested for reactivities to a panel of PCV2 positive sera from infected piglets. Among the more than 50 candidate peptide antigens tested, the PCV2 Cap1 antigenic peptide (SEQ ID NO. 1), was found to have a cluster of immunodominant B cell epitopes and had the most significant and consistent antigenicity for the PCV2 positive serum panel. The Cap1 peptide also was proven to be of high immunogenicity when tested in a trial of vaccines comprising this peptide sequence. The production and use of vaccines comprising a PCV2 Cap1 antigenic/immunogenic peptide (e.g., SEQ ID NO: 1) are within the scope of various exemplary embodiments of the invention.

Specific embodiments of the PCV2 Cap1 immunogenic/antigenic peptide invention are further defined as being immunologically functional homologues of SEQ ID NO: 1 that have corresponding sequences and conformational elements from mutant and variant strains of PCV2. Homologous PCV2 Cap1 antigenic peptides have amino acid residues that correlate approximately with capsid protein positions 47-202 of the originating variant PCV2 strains. Such homologues are readily demonstrated through sequence alignment programs such as ClustalW (produced by Julie D. Thompson, Toby Gibson of European Molecular Biology Laboratory, Germany and Desmond Higgins of European Bioinformatics Institute, Cambridge, UK. Algorithmic). Table 2 shows the alignment by ClustalW of eleven Cap1 antigen sequences taken from diverse strains of PCV2 identified by GenBank Accession numbers. The originating PCV strains of the Cap1 homologues aligned in Table 2 include viruses of genotypes 2a, 2b, 2d, 1/2a, and these diverse strains were isolated from animals in Taiwan, China, U.S.A, Canada, Brazil, Spain, Germany and Denmark. Table 2 also exemplifies a homologue as being a consensus Cap1 sequence wherein the amino acids assigned to the variable positions are those most frequently applied for those positions. In one embodiment, the homologue has an amino acid sequence from about amino acid position 47 to about amino acid position 202 of a PCV2 capsid protein.

Homologues of the invention are further defined as having at least 80% identity to SEQ ID NO: 1. In one embodiment, the variant strain homologue has at least 85% identity to SEQ ID NO: 1. In another embodiment, the variant strain homologue has at least 90% identity to SEQ ID NO: 1. In yet another embodiment, the variant strain homologue has at least 95% identity to SEQ ID NO: 1.

Other embodiments of the invention provide for immunologically functional analogues of the PCV2 Cap1 antigenic peptide. An immunologically functional analogue of the Cap1 peptide includes variants of SEQ ID NO: 1 and homologues which retain substantially the same antigenicity and immunogenicity as the original antigenic peptide. For example, variants that are functional analogues of SEQ ID NO: 1 or of a homologue can have a conservative substitution in an amino acid position; a change in overall charge; a covalent attachment to another moiety; or small additions, insertions, deletions or conservative substitutions and/or any combination thereof. Thus, antibodies that bind to a PCV2 Cap1 antigenic peptide (e.g., SEQ ID NO: 1) will also bind to the immunologically functional analogues of that PCV2 Cap1 antigenic peptide with substantially similar efficacy. In one embodiment, the functional analogue has at least 50% identity to SEQ ID NO: 1 or homologue. In another embodiment, the functional analogue has at least 80% identity to SEQ ID NO: 1 or homologue. In yet another embodiment, the functional analogue has at least 85% homology to SEQ ID NO: 1 or homologue. In still another embodiment, the functional analogue has at least 90% homology to SEQ ID NO: 1 or homologue.

In one embodiment, immunologically functional analogues of the PCV2 Cap1 antigenic peptide encompasses versions of PCV2 Cap1 antigenic peptide that have been modified by conservative substitutions, and by insertions or deletions. In this embodiment, immunologically functional analogues can be modified from SEQ ID NO: 1 or from a homologue of SEQ ID NO: 1 by substitutions that are conservative.

Conservative substitutions are when one amino acid residue is substituted for another amino acid residue with similar chemical properties. For example, the nonpolar (hydrophobic) amino acids include alanine, leucine, isoleucine, valine, proline, phenylalanine, tryptophan and methionine; the polar neutral amino acids include glycine, serine, threonine, cysteine, tyrosine, asparagine, and glutamine; the positively charged (basic) amino acids include arginine, lysine and histidine; and the negatively charged (acidic) amino acids include aspartic acid and glutamic acid.

In another embodiment, immunologically functional analogues can be modified by amino acid additions to the N-terminus, C-terminus, and/or by insertions into the middle of the peptide. In various embodiments of the invention, additions are to the N-terminus or C-terminus of the peptide. Additions can be of 1, 2, 3, 4, 5, 6, 7, 8, 9, 10, 11, 12, 13, 14, 15, 16, 17, 18, 19, or 20 amino acid residues. Such additions may constitute amino acid sequences which are not present in PCV2 capsid and which do not alter the immunogenicity of the PCV2 capsid portion of the peptide. Additions which are not present in PCV2 capsid include, but are not limited to, small charged sequences (e.g., lysine-lysine-lysine), amino acids that enable the formation of branched structures (e.g., ϵN-lysine) or enable the formation of cyclized structures (e.g., cysteine). In an embodiment of the invention, additions of amino acid sequences that are not present in PCV2 Cap1 are of 5 amino acids or less Amino acid additions can be either classical or non-classical amino acids or a mixture thereof.

In another specific embodiment, immunologically functional analogues can be modified by amino acid deletions to the N-terminus, C-terminus, and/or middle of the peptide. In various embodiments, deletions are to the N-terminus or C-terminus of the peptide. Deletions can be of 1, 2, 3, 4, 5, 6, 7, 8, 9, 10, 11, 12, 13, 14, 15, 16, 17, 18, 19, or 20 amino acid residues. In a specific embodiment, deletions of amino acid sequences are of 10 amino acids or less.

In another embodiment, immunologically functional analogues of PCV2 Cap1 antigenic peptide encompass PCV2 cap antigenic peptides that have been modified by an alteration in charge. Such alteration in charge may be the result of amino acid substitutions, additions, or deletions, or the covalent attachment of a charged molecule. The alteration in charge may have the result of making the peptide more basic, more acidic, or more neutral as compared to the unmodified peptide. In a specific embodiment, the peptide is made more basic by the addition of 1-5 lysine residues to the N-terminus or C-terminus In a more specific embodiment, the peptide is made more basic by the addition of 3 lysine residues to the N-terminus.

By way of a non-limiting example, immunologically functional analogues of the peptide of the invention can have from 1 to about 5 additional amino acids (classical and non-classical) added to the terminal amino acids. For example, the sequence Lys-Lys-Lys can be added to the amino terminus of this PCV2 Cap1 peptide for a change in charge.

The peptides can be readily synthesized using standard techniques, such as the Merrifield solid phase method of synthesis and the myriad of available improvements on that process. The peptides can also be made using recombinant DNA technology. As such, nucleic acid molecules encoding the PCV2 Cap1 antigenic peptide and immunologically functional analogues of the PCV2 Cap1 antigenic peptide and compliments thereof are encompassed by various exemplary embodiments of the invention. Vectors, especially expression vectors, comprising the nucleic acid molecules encoding PCV2 Cap1 antigenic peptides and immunologically functional analogues are also encompassed by various exemplary embodiments of the invention. Host cells containing the vectors are also encompassed by various exemplary embodiments of the invention.

Various exemplary embodiments of the invention also encompass methods of producing the PCV2 Cap1 antigenic peptide and immunologically functional analogues of the PCV2 Cap1 antigenic peptide. For example, the method can comprise incubating a host cell containing an expression vector comprising a nucleic acid molecule encoding a PCV2 Cap1 antigenic peptide and/or immunologically functional analogue of an PCV2 Cap1 antigenic peptide under such conditions that the PCV2 Cap1 peptide and/or immunologically functional analogue of a PCV2 Cap1 peptide is expressed. This embodiment can use controlled and well-defined immunogens derived from the lysates or secretions of such cells.

One embodiment of the invention provides peptide compositions produced by solid-phase synthesis. The quality of antigens produced by the chemical process of this embodiment are controlled and defined and, as a result, reproducibility of antigenicity, immunogenicity and yield can be assured. Also, no biohazardous materials are used in the manufacture of peptide antigens, reducing risks and eliminating the need for expensive biological containment. As site-specific immunogens presenting high molar concentrations of selected epitopes, both the safety and immunopotency of the vaccine employing PCV2 Cap1 antigenic peptide compositions are assured.

In one embodiment, the peptides of the invention are synthesized. The use of defined Cap1 synthetic peptides minimizes the false-positive results when used as antigen for antibody detection and diagnosis in piglets. The use of defined synthetic peptides, having known B cell and Th epitopes, as immunogens eliminates the undesired non-PCV2-specific immune responses caused by the presence of antigenic materials originating from PCV2-infected or recombinant virus-infected host cells and from recombinant protein expression systems that may be co-purified with PCV2 virus and/or recombinant proteins, when used as the immunogenic ingredients of a vaccine. For example, sera from pigs may have antibodies to host cells, or to recombinant *Escherichia coli*, yeast or baculovirus which are then cross-reactive with the antigenic materials used in diagnostic tests based on the biologically-derived antigens, and such immune responses generated by vaccines having these extraneous immunogens as ingredients will be non-protective. In contrast, pigs receiving a PCV2 Cap1 peptide vaccine of the invention will generate focused immune responses devoid of untoward antibodies and other immune responses to proteins originating from host cells or expression vectors, e.g., proteins from recombinant *Escherichia coli*, yeast or baculovirus that had been co-purified with the biologically-derived PCV2 antigens.

This embodiment of synthetic peptides also minimizes interference from impurities that are generated during production. With long syntheses, despite the rigorous control of coupling efficiency, peptide analogues are also produced due to events during elongation cycles, including amino acid insertion, deletion, substitution, and premature termination, thus yielding to the generation of multiple peptide analogues along with the targeted peptide syntheses. Nonetheless, such peptide analogues are still suitable in peptide preparations as contributors to antigenicity and immunogenicity when used in immunological application either as solid phase antigen for purpose of immunodiagnosis or as immunogen for purpose of vaccination.

During 25 years of experience in immunological applications of synthetic peptides, we have found that the range in structural variability that allows for retention of an intended immunological activity is far more accommodating than the range in structural variability allowed for retention of a specific drug activity by a small molecule drug or the desired activities and undesired toxicities found in large molecules that are co-produced with biologically-derived drugs. This is why peptide analogues, either intentionally designed or inevitably produced by errors of the synthetic process as a mixture of deletion sequence byproducts that have chromatographic and immunologic properties similar to the intended peptide, are frequently as effective as a purified preparation of the desired peptide. Designed analogues and unintended analogue mixtures are effective as long as a discerning QC procedure is developed to monitor both the manufacturing process and the product evaluation process so as to guarantee the reproducibility and efficacy of the final products employing these peptides.

In other embodiments of the invention, Th peptides are included in the vaccine compositions. The presence of Th peptides can improve immunogenicity of the PCV2 Cap1 peptide vaccine. PCV2 Cap1 peptides (including the homologues and analogues described above) can be covalently linked to and/or mixed with Th epitopes.

In one embodiment, Th peptides having clusters of immunodominant PCV2 Th epitopes from ORF 1 and ORF 3, described as SEQ ID NOS: 3-5 (also shown in Table 1) and unlinked to the Cap1 immunogen, can be used to supplement the immunogenicity of PCV2 Cap1 peptide vaccines. Including SEQ ID NOS: 3-5 as free peptides, without covalent linkages, can improve immunogenicity of the vaccine formulations.

In another embodiment, PCV2 Cap1 peptides (including homologues and analogues described above) can be covalently linked, with or without a spacer, to a peptide containing a sequence known to contain a Th epitope. This embodiment can offer enhanced immunogenicity over the equivalent Cap1 immunogens without the covalently linked Th epitope. In a specific embodiment, the peptide containing the Th epitope is covalently linked to the N-terminus and/or C-terminus of the PCV2 peptide. In another specific embodiment, the spacer has the sequence Lys-Lys-Lys-ϵNLys (SEQ ID NO: 7), also shown in Table 1. In an embodiment, the peptide containing the Th epitope is covalently linked to the amino terminus of the PCV2 Cap1 peptide. In a specific embodiment, the peptide containing the Th epitope is the artificial combinatorial Th peptide SEQ ID NO:2 (as shown in Table 1) linked to the amino terminus through a Lys-Lys-Lys-ϵNLys spacer, and presented as SEQ ID NO: 6 (also shown in Table 1).

Various embodiments of the invention relate to vaccine compositions for protecting pigs against PCV2. In exemplary embodiments, the vaccine comprises an immunogenic peptide antigen and an acceptable delivery vehicle or adjuvant. In various embodiments, the PCV2 vaccine composition, comprises a peptide antigen and a veterinarily acceptable delivery vehicle or adjuvant, wherein the peptide antigen comprises an amino acid sequence selected from the group consisting of:

a) from about amino acid position 47 to about amino acid position 202 of a PCV2 capsid protein;
b) SEQ ID NO: 1;
c) a homologue of (b);
d) an antigenically and immunologically functional analogue of (a), (b), or (c);
e) (a), (b), (c), or (d) having at least one conservative amino acid substitution, amino acid addition, and/or amino acid deletion; and
f) any combination of (a)-(e).

In an embodiment of the PCV2 vaccine, the charge of the peptide antigen is altered by adding or deleting 1 to 5 amino acids. In another embodiment of the PCV2 vaccine, the antigenically and immunologically functional homologue or analogue has at least 80% identity to the antigen of the amino acid sequence that is approximately positions 47-202 of a PCV2 capsid protein. In a particular embodiment, the peptide antigen has an amino acid sequence selected from the group consisting of SEQ ID NOs 9, 10, 11, 12, 13, 14, 15, 16, 17, 18, 19, and 20.

In another embodiment of the PCV2 vaccine the peptide antigen further comprises a T helper epitope covalently linked to the N-terminus or C-terminus of the peptide antigen. In a specific embodiment, the T helper epitope is covalently linked to the amino terminus of the peptide antigen. In another specific embodiment, the T helper epitope is covalently linked to the peptide antigen through a spacer having at least one amino acid. In a particular embodiment, the T helper epitope is SEQ ID NO: 2. In yet another particular embodiment, the spacer is SEQ ID NO: 7. In a specific embodiment, the peptide antigen is SEQ ID NO: 1 or SEQ ID NO: 6.

In various exemplary embodiments, any amount of immunogenic peptide antigen can be used to elicit immune responses in the animal. In a particular embodiment, the amount of peptide antigen is between about 0.1 μg to about 100 mg. In another particular embodiment, the amount of peptide antigen is between about 1 μg to about 10 mg. In yet another embodiment, the amount of peptide antigen is between about 10 μg to about 1 mg.

In various embodiments of the PCV2 vaccine composition the composition further comprises an equimolar mixture of three PCV2 T helper epitope peptides of SEQ ID NOS: 3, 4, and 5. In a specific embodiment, the amount of the equimolar mixture of SEQ ID NOS: 3, 4, and 5 is between about 0.1 μg to about 1 mg. In a more specific embodiment, the amount of the equimolar mixture of SEQ ID NOS: 3, 4, and 5 is between about 1 μg to about 100 μg.

In various exemplary embodiments, any type or amount of delivery vehicle or adjuvant can be used. In a particular embodiment, the delivery vehicle and adjuvant is Montanide™ ISA 50V2 (an oil vaccine adjuvant composition comprised of mineral oil and mannide oleate for production of water-in-oil emulsions), Tween® 80 (also known as: Polysorbate 80 or Polyoxyethylene (20) sorbitan monooleate), a CpG oligonucleotide, and/or any combination thereof.

In a specific embodiment, the PCV2 vaccine composition, comprises a peptide antigen of SEQ ID NO: 6 and a veterinarily acceptable delivery vehicle or adjuvant, wherein the amount of peptide antigen is between about 10 μg to about 1 mg.

Another embodiment of the invention relates to a method for protecting piglets that are or are not PCV2 MDA positive against PCV2 infection, comprising administering a vaccine encompassed by any of the exemplary embodiments as described above.

A PCV2 Cap1 peptide prepared in accordance with the present disclosure can also be used to detect PCV2 antibodies by using the peptide in an antigenically effective amount in the capture phase of an immunoassay, e.g., in the solid phase immunosorbent of ELISA test kits. In accordance with an embodiment of the present invention, any compatible immunoassay format can be used with the subject peptides. Such formats are well known to the ordinarily skilled artisan and have been described in many standard immunology manuals and texts, see for example Harlow et al. 1988 (26). These include, among other well-known immunoassay formats, an enzyme-linked immunoadsorbent assay (ELISA), an enzyme immunodot assay, an agglutination assay, an antibody-peptide-antibody sandwich assay, a peptide-antibody-peptide sandwich assay. In an embodiment, the immunoassay is an ELISA using a solid phase coated with a PCV2 Cap1 peptide composition.

According to one embodiment of the invention, the peptide is capable of testing sera from sows and gilts, boars and barrows, and piglets for PCV2 infection by a screening ELISA, for the evaluation of sera from pre-vaccinated piglets for levels of maternally derived anti-PCV2 antibodies, and for determining the levels of immune responses in vaccinated piglets towards a vaccine employing PCV2 Cap1 antigenic peptide, full-length capsid protein, or inactivated PCV2 virions.

In a specific embodiment, an ELISA immunoassay can be used to test swine blood, serum or plasma samples for the presence of anti-PCV2 antibodies comprising the steps of:

i. attaching a PCV2 Cap1 peptide to a solid support,
ii. exposing said peptide attached to said solid support to a swine blood, serum or plasma sample containing antibodies, under conditions conducive to binding of the antibody to the peptide, and iii. detecting the presence of antibodies bound to said peptide attached to said solid support.

In an exemplified use of the subject ELISA kit, a pig serum sample to be tested is diluted in sample diluent and then contacted with one or more of the PCV2 Cap1 peptides described above for a time and under conditions for any antibodies, if present, to bind to the peptide-sensitized solid phase. After removal of unbound material (e.g., by washing with phosphate-buffered-saline), the secondary complex is contacted with labeled antibodies to pig-specific IgG or labeled protein A, protein G, or protein A/G. These antibodies or proteins A, G or A/G bind to the secondary complex to form a tertiary complex and, since the second antibodies or proteins A, or G or A/G are labeled with a reporter molecule, when subjected to a detecting means, the tertiary complex is detected. The reporter molecule can be an enzyme, radioisotope, fluorophore, bioluminescent molecule, chemiluminescent molecule, biotin, avidin, streptavidin or the like. For ELISA the reporter molecule is preferably an enzyme.

The following examples serve to illustrate the present invention and are not to be used to limit the scope of the invention.

TABLE 1

Amino acid sequences of PCV2 immunogenic peptides derived from PCV2 ORF1, ORF2 and ORF3 proteins, and an artificial combinatorial Th peptide for enhancement of ORF2 Cap1 peptide immunogenicity. Combinatorial sequences are shaded.

| | |
|---|---|
| B cell epitope cluster peptide derived from PCV2 ORF2 capsid protein (Cap1 peptide) | |
| TRLSRTFGYTVKATTVRTPSWAVDMMRFNISDFVPPGGGTNKISIPFEYYRIRKVKVEFWPCSPITQGDRGVGSTAVILDDNFVT KATALTYDPYVNYSSRHTIPQPFSYHSRYFTPKPVLDSTIDYFQPNNKRNQLWLRLQTSANVDHVGLGT | (SEQ ID No. 1) |
| Artificial combinatorial Th peptide (UBITh3) | |
| ISISEIKGVIVHKIETILF<br>  T RT    TR | (SEQ ID NO. 2) |
| T helper epitope cluster peptides derived from PCV2 ORF 1 Rep protein | |
| CHIEKAKGTDQQNKEYCSKE | (SEQ ID No. 3) |
| KWWDGYHGEEVVVIDDFYGW | (SEQ ID NO. 4) |
| T helper epitope cluster peptide derived from PCV2 ORV3 Apo protein | |
| PRWPHNDVYIGLPITLLHFP | (SEQ ID No. 5) |
| B cell epitope cluster peptide derived from PCV2 ORF2 capsid protein (Cap1 peptide) linked through spacer to artificial combinatorial Th peptide (UBITh3) | |
| ISISEIKGVIVHKIETILF-KKεKK-TRLSRTFGYTVKATTVRTPSWAVDMMRFNISDFVPPGGGTNKISIPFEYYRIRKVKVE<br>  T RT    TR<br>FWPCSPITQGDRGVGSTAVILDDNFVTKATALTYDPYVNYSSRHTIPQPFSYHSRYFTPKPVLDSTIDYFQPNNKRNQLWLRLQT SANVDHVGLGT | (SEQ ID No. 6) |

TABLE 2

Alignments for homologous Cap1 sequences from various PCV2 strains and a consensus. Variable positions are shaded.

| Access No. | Country* | 47 … 130 |
|---|---|---|
| ACC59783 | US | TRLSRTFGYTIKRTTVRTPSWAVDMMRFNINDFLPPGGGSNPRSVPFEYYRIRKVKVEFWPCSPITQGDRGVGSSAVILDDNFV |
| ACQ99546 | DK | TRLSRTFGYTIKRTTVKTPSWAVDMMRFNINDFLPPGGGSNPRSVPFEYYRIRKVKVEFWPCSPITQGDRGVGSSAVILDDNFV |
| ACX47360 | DE | TRLSRTFGYTIKRTTVKTPSWAVDMMRFNINDFLPPGGGSNPRSVPFEYYRIRKVKVEFWPCSPITQGDRGVGSSAVILDDNFV |
| ACV53396 | ES | ----RTFGYTVKRTTVRTPSWAVDMMRFNINDFLPPGGGSNPRSVPFEYYRIRKVKVEFWPCSPITQGDRGVGSSAVILDDNFV |
| ADI44325 | CN | TRLSRTIGYTVKKTTVRTPSWNVDMMRFNINDFLPPGGGSNPRSVPFEYYRIRKVKVEFWPCSPITQGDRGVGSTAVILDDNFV |
| ADD25772 | CN | TRLSRTIGYTVKKTTVRTPSWNVDMMRFNINDFLPPGGGSNPRSMPFEYYRIRKVKVEFWPCSPITQGDRGVGSTAVILDDNFV |
| ADB97547 | CN | ARLSRTFGYTVKRTTVTTPSWAVDMMRFKLDDFVPPGGGSNPRSIPFEYYRIRKVKVEFWPCSPITQGDRGVGTTAVILDDNFV |
| ABW76695 | BR | TRLSRTFGYTVKRTTVTTPSWAVDMMRFKLDDFVPPGGGSNPRSIPFEYYRIRKVKVEFWPCSPITQGDRGVGTTAVILDDNFV |
| ABI29888 | US | ARLSRTFGYTVKATTVSTPSWAVDMMRFNLDDFVPPGGGSNPRSIPFEYYRIRKVKVEFWPCSPITQGDRGVGSSAIILDDNFV |
| YP_003422531 | CA | TRLSRTFGYTVKATTVRTPSWAVDMMRFNIDDFVPPGGGSNPRSIPFEYYRIRKVKVEFWPCSPITQGDRGVGSTAVILDDNFV |
| AAN62766 | TW | TRLSRTFGYTVKATTVRTPSWAVDMMRFNINDFVPPGGGSNPRSIPFEYYRIRKVKVEFWPCSPITQGDRGVGSTAVILDDNFV |
| consensus | | TRLSRTFGYTVKRTTVRTPSWAVDMMRFNINDFLPPGGGSNPRSIPFEYYRIRKVKVEFWPCSPITQGDRGVGSTAVILDDNFV |

| Access No. | Country* | 131 … 200 | SEQ ID NO |
|---|---|---|---|
| ACC59783 | US | TKATALTYDPYVNYSSRHTITQPFSYHSRYFTPKPVLDSTIDYFQPNNKRNQLWLRLQTAGNVDHVGLGT | 9 |
| ACQ99546 | DK | TKATALTYDPYVNYSSRHTITQPFSYHSRYFTPKPVLDSTIDYFQPNNKRNQLWLRLQTAGNVDHVGLGT | 10 |
| ACX47360 | DE | TKATALTYDPYVNYSSRHTITQPFSYHSRYFTPKPVLDSTIDYFQPNNKRNQLWMRLQTSRNVDHVGLGT | 11 |
| ACV53396 | ES | TKATALTYDPYVNYSSRHTITQPFSYHSRYFTPKPVLDSTIDYFQPNNKRNQLWLRLQTAGNVDHVGLGT | 12 |
| ADI44325 | CN | TKANALTYDPYVNYSSRHTITQPFSYHSRYFTPKPVLDRTIDYFQPNNKRNQLWLRLQTTGNVDHVGLGT | 13 |
| ADD25772 | CN | TKANALTYDPYVNYSSRHTITQPFSYHSRYFTPKPVLDRTIDYFQPNNKRNQLWLRLQTTGNVDHVGLGT | 14 |
| ADB97547 | CN | PKANALTYDPYVNYSFRHTIPQPFSYHSRYFTPKPVLDSTIDYFQPNNKRNQLWMRIQTSGNVDHVGLGT | 15 |
| ABW76695 | BR | PKANALTYDPYVNYSSRHTIPQPFSYHSRYFTPKPVLDSTIDYFQPNNKKNQLWLRLQTSRNVDHVGLGT | 16 |
| ABI29888 | US | IKATAQTYDPYVNYSSRHTIPQPFSYHSRYFTPKPVLDSTIDYFQPNNKRNQLWMRLQTSRNVDHVGLGT | 17 |
| YP_003422531 | CA | TKATALTYDPYVNYSSRHTIPQPFSYHSRYFTPKPVLDSTIDYFQPNNKRNQLWMRLQTSRNVDHVGLGT | 18 |
| AAN62766 | TW | TKATALTYDPYVNYSSRHTIPQPFSYHSRYFTPKPVLDSTIDYFQPNNKRNQLWLRLQTSANVDHVGLGT | 19 |
| Consensus | | TKATALTYDPYVNYSSRHTITQPFSYHSRYFTPKPVLDSTIDYFQPNNKRNQLWLRLQTSANVDHVGLGT | 20 |

*US - United States of America, DK - Denmark, DE - Germany, ES - Spain, CN - China, BR - Brazil, CA - Canada, TW - Taiwan

EXAMPLE 1

Immunofluorescence Assay Using Capsid Protein Inside the Nucleus of Co-Transfected HTK Cells for Detection of Antibodies to PCV2

Antibodies directed against PCV2 can be detected by immunofluoresence using HTK cells co-transfected with PCV2 capsid protein. This method provides for transient expression of full length PCV2 capsid antigen in the HTK cells. This immunoassay method also provides for capsid protein expression through recombinant virus infection, while ensuring preservation of native capsid protein conformation during synthesis and maturation stages, providing conditions for antibody detection of high specificity and sensitivity.

HTK cell line cells were infected with T7 polymerase recombinant vaccinia virus (T7/vac) (22), and co-transected with the pCR-orf2 plasmid by Lipofectamine™ (Invitrogen) (23) according to the mechanism illustrated in FIG. 1A. Specifically, construction of the pCR-orf2 plasmid for expression of the native PCV2 capsid protein mediated by the T7 polymerase promoter was accomplished as follows: A full length of PCV2 ORF2 gene (from Taiwan PCV2 strain Cyc08; Accession No. AAN62766 with an N→S mutation at position 77) was amplified by polymerase chain reaction (PCR) and cloned into the pCR®2.1-TOPO® plasmid vector (Invitrogen). The expression ability of the pCR-orf2 plasmid was confirmed by sequencing which shows the full nucleotide sequence for ORF2 from PCV2 strain Cyc08 (23).

HTK cells were grown to 80% confluence in 96-well plates, infected with T7 polymerase recombinant vaccinia virus (T7/vac) (22), and then co-transected with the pCR-orf2 plasmid by Lipofectamine™ (Invitrogen). The pCR-orf2 plasmid co-transfected cells were found to reliably express PCV capsid antigen within the nucleus of HSK cells and thus were suitable to be used for the capture and detection of antibodies to PCV2 capsid protein through immunofluorescence assay (IFA).

Titration of PCV2 Antibody by Immunofluorescence Assay (IFA).

Figure 1B:
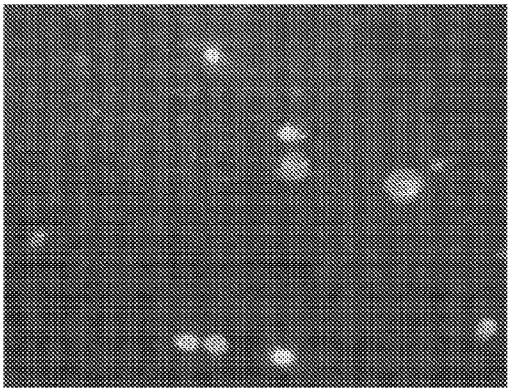

Plates with native PCV2 capsid protein as antigen were prepared in batch by coating with the transfected HTK cells, and stored at −80° C. Antigen coated plates were prepared in batches of 100 each time to ensure quality control. Serum samples were initially diluted 50-fold in PBS followed by a 2-fold serial dilution series. For each test run, a positive control serum from a PCV2-infected SPF pig and negative control serum from an uninfected SPF pig were both included to validate the expression of the capsid protein by the pCR-orf2 plasmid within the nuclei of the HSK cells. Serum samples giving fluorescence signals localized to the nuclei (as shown in FIG. 1B) at dilutions higher than 1:50 were scored as having IFA titers >50; and these titers were indicative of animals infected by PCV2 or of animals having developed anti-PCV antibodies as a result of vaccination. Observation by IFA can also facilitate the differentiation of true positive antibody signals from false positive signals by distinguishing specific nucleus-localized anti-capsid antibody binding from non-specific protein binding.

All testing of serum samples collected from either pigs with natural infection or from pigs given PCV2 Cap1 peptide-based vaccine were performed under code.

EXAMPLE 2

ELISA Method for Detection of Serum Antibodies for Identification of Naturally PCV2-Infected Pigs and Pigs Given Cap1 Peptide-Based PCV2 Vaccines The wells of 96-well plates were coated separately for 1 hour at 37° C. with 100 μL of individual PCV2 capsid peptides, e.g., peptide of SEQ ID NO.:1 (PCV2 Cap1 peptide), at 2 μg/mL in 10 mM $NaHCO_3$ buffer, pH 9.5 unless noted otherwise.

The peptide-coated wells were incubated with 250 μL of 3% by weight of gelatin in PBS in 37° C. for 1 hour to block non-specific protein binding sites, followed by three washes with PBS containing 0.05% by volume of TWEEN® 20 and dried. Pig serum positive for PCV2 antibody by IFA and negative control sera were diluted 1:20, unless otherwise noted, with PBS containing 20% by volume normal goat serum, 1% by weight gelatin and 0.05% by volume TWEEN® 20. One hundred microliters of the diluted specimens were added to each of the wells and allowed to react for 60 minutes at 37° C.

The wells were then washed six times with 0.05% by volume TWEEN® 20 in PBS in order to remove unbound antibodies. Horseradish peroxidase-conjugated goat anti-swine IgG was used as a labeled tracer to bind with the antibody/peptide antigen complex formed in positive wells. One hundred microliters of the peroxidase-labeled goat anti-swine IgG at a pre-titered optimal dilution and in 1% by volume normal goat serum with 0.05% by volume TWEEN® 20 in PBS, was added to each well and incubated at 37° C. for another 30 minutes. The wells were washed six times with 0.05% by volume TWEEN® 20 in PBS to remove unbound antibody and reacted with 100 μL of the substrate mixture containing 0.04% by weight 3',3',5',5'-Tetramethylbenzidine (TMB) and 0.12% by volume hydrogen peroxide in sodium citrate buffer for another 15 minutes. This substrate mixture was used to detect the peroxidase label by forming a colored product. Reactions were stopped by the addition of 100 μL of 1.0M $H_2SO_4$ and absorbance at 450 nm ($A_{450}$) determined.

Serum dilutions were done in accordance with the purpose for detecting PCV2 antibodies in the animal sera: (a) For identification of potential natural infection, a dilution of 1:20 was used, the $A_{450}$ reading was recorded, and a built-in intrinsic negative control for cutoff calculation was used; or (b) For the determination of antibody titers of pigs that received peptide-based PCV2 vaccine formulations, 10-fold serial dilutions of sera from 1:10 to 1:10,000 were tested, and the titer of a tested serum, expressed as $Log_{10}$, was calculated by linear regression analysis of the $A_{450}$.

The serological validity of the Cap1-based ELISA for detection of PCV2 infection was confirmed by the high correlation coefficient (0.782 shown in Table 3) between the results for the ELISA and for the highly specific native capsid-based IFA (Example 1).

EXAMPLE 3

Site-Specific Serology for Identification of Optimal PCV2 Capsid Peptides for Use in Both Vaccine and Diagnostic Applications The genomic sequences of PCV2 from the previously published sequence of PCV2 isolate 1010-Stoon (2) and from a Taiwan strain Cyc08 were used to deduce the protein sequences from open reading frames, and the data obtained from the two ORF2 sequences were used to design candidate peptide antigens for immunological testing. Over 70 capsid peptides with overlapping sequences of lengths from about 20 to over 170 amino acids were designed and synthesized for serological validation, with an aim to identify antigenic peptides that are targets for B and T cell recognition associated with PCV2 infection. Capsid peptides having optimal B cell epitopes were then identified by a process of serological validation. This method for epitope mapping with long and short peptides identifies discontinuous conformational epitopes as well as linear epitopes (24, 25). A panel of 24 sera characterized with respect to anti-PCV2 capsid protein reactivities by the IFA test described in Example 1 was used for the serological validation of the peptides. The sera were used to screen the overlapping PCV2 capsid peptides for strong and consistent antigenicities that could be useful for diagnosis and for prediction of antibody-mediated protective immunogenicities. The sera used to construct this PCV2 reactivity panel were collected from pigs in the field found to have natural infection or from normal and SPF pigs known to be free of PCV2 infection, each having had their respective anti-PCV2 capsid protein reactivity titered by IFA as shown in Table 3.

TABLE 3

Sera from piglets with or without PCV2 infection used for the serological validation of Cap1 peptide ELISA by correlation to capsid IFA titers

| Swine Serum Code | Host description | IFA titer | Cap1 Peptide ELISA ($A_{450}$) |
|---|---|---|---|
| RS 3 | SFP | <50 | 0.251 |
| RS 4 | SFP | <50 | 0.204 |
| RS 6 | SFP | <50 | 0.134 |
| RS 8 | SFP | <50 | 0.284 |
| RS 9 | SFP | <50 | 0.285 |
| RS 10 | SFP | <50 | 0.192 |
| RS 12 | SFP | <50 | 0.179 |
| RS 13 | SFP | <50 | 0.171 |
| RS 15 | SFP | <50 | 0.233 |
| NS 5 | Normal serum | <50 | 0.123 |
| NS 6 | Normal serum | <50 | 0.140 |
| NS 9 | Normal serum | <50 | 0.245 |
| RS 28 | Field | 200 | 0.259 |
| RS 24 | Field | 400 | 0.354 |
| RS 25 | Field | 800 | 0.528 |
| RS 26 | Field | 800 | 0.479 |
| RS 1 | SFP | 1600 | 0.794 |
| RS 39 | Field | 1600 | 0.492 |
| RS 7 | SFP | 3200 | 0.633 |
| RS 16 | SFP | 3200 | 1.129 |
| RS 42 | PCV2-infected | 3200 | 3.000 |
| RS 43 | PCV2-infected | 3200 | 2.782 |
| RS 41 | PCV2-infected | 6400 | 3.000 |
| RS 45 | PCV2-infected | 12800 | 2.657 |
| Correlation coefficient | | 0.782 | |

A panel including 12 PCV2 IFA positive (IFA titer >1:50) swine sera and 12 PCV2 IFA negative (titer <1:50) swine sera was used for serological validation of the PCV2 Cap1 (SEQ ID NO: 1) peptide-based ELISA. Sera were diluted 1:21 for ELISA testing. A correlation coefficient of 0.782 was found between IFA titers and the $A_{450}$ readings from the peptide-based ELISA.

Among the overlapping peptides, short peptides comprising about 20 amino acids were synthesized by an Applied BioSystems Inc. automated peptide synthesizer Model 433 (Lexington, Ky.); and longer peptides comprising from about 25 up to about 170 amino acids were synthesized using Applied BioSystems Peptide Synthesizer Models 430A, 431 and 433, using Fmoc chemistry.

Each peptide was produced by an independent synthesis on a solid-phase support, with Fmoc protection for the terminus and side chain protecting groups of trifunctional amino acids. Completed peptides were cleaved from the solid support and side chain protecting groups removed by 90% trifluoroacetic acid. Synthetic peptide preparations were characterized for correct composition by Matrix-Assisted Laser Desorption Time-Of-Flight (MALDTOF) Mass Spectrometry, and for content including synthesis profile, content and concentration by Reverse Phase HPLC. With long syntheses, despite the rigorous control of coupling efficiency, peptide analogues were also produced due to events during elongation cycles, including amino acid insertion, deletion, substitution, and premature termination, thus yielding to the generation of multiple peptide analogues along with the targeted peptide syntheses. Nonetheless, such peptide analogues were still suitable in peptide preparations as contributors to antigenicity and immunogenicity when used in immunological application either as solid phase antigen for purpose of immunodiagnosis or as immunogen for purpose of vaccination. Typically, such peptide analogues, either intentionally designed or generated through synthetic process as a mixture of byproducts, are frequently as effective as a purified preparation of the desired peptide, as long as a discerning QC procedure is developed to monitor both the manufacturing process and the product evaluation process for guaranteeing the reproducibility and efficacy of the final products employing these peptides.

Antigenicities of the synthesized peptides of varied lengths were tested for initial reactivity profiles with the serum panel. The antibodies present in the serum panel from the naturally infected pigs followed a trend of increasing reactivities to PCV2 capsid peptides of increasing lengths. As a consequence of extensive serological screening data acquired with the sera in the lower panel of Table 3, a long capsid peptide designated as "Cap1" (SEQ ID NO: 1) of length 154 amino acids, provided for an unusually sensitive ELISA. The Cap1 peptide also imparted high specificity to this ELISA as shown in the upper panel of Table 3 by low reactivities with the IFA-validated negative pig sera. In fact, the predominant serological reactivities of the PCV-infected pigs were associated only with the Cap1 154 mer peptide (SEQ ID NO. 1). It is therefore reasonable to assume that a majority of the serological reactivities present in the PCV2-infected pigs are due to antibodies recognizing clusters of B cell epitopes that were present only on the long peptide. Furthermore, the unexpected immunodominant antigenicity of the 154 mer is consistent with the long peptide representing a large exposed surface on the capsid protein that presents processions of long continuous and discontinuous epitopes. These epitopes comprise B cell epitopes that are linked to T helper cell (Th) epitopes requisite for the stimulation of the B cell antibody responses.

EXAMPLE 4

Immunizations of Guinea Pigs with Vaccines Formulated with PCV2 Cap1 Peptide for Initial Immunogenicity Evaluation and Correlation of Antibody Titers in Vaccines by Cap1 Peptide-Based ELISA and Native Capsid-Based IFA Guinea Pig Immunization.

In an exemplified use of vaccines of the invention, vaccines having as immunogens peptides comprising the Cap1 antigenic peptide without linkage to a foreign Th epitope (for example SEQ ID NO: 1) or with covalent linkage through the amino terminus and a Lys-Lys-Lys-ϵNLys (SEQ ID NO: 7) spacer to a foreign T helper epitope such as UBITh®3 (SEQ ID NO: 2), for example SEQ ID NO: 6, were formulated into water-in-oil emulsions using a commercially available oil vaccine delivery vehicle, Montanide™ ISA 50V2. Two groups of guinea pigs were immunized with the peptide-based vaccines as shown in Table 4.

This was an initial study conducted in small animals to evaluate the immunogenicity of the Cap1 peptide (SEQ ID NO: 1) with and without covalent linkage to a foreign T helper site, UBITh®3 (SEQ ID NO: 2), in a commonly used water-in-oil emulsion formulation to obtain a serum panel with a range of antibody responses. The unlinked Cap1 peptide is designated as SEQ ID NO: 1 (Table 1). The Cap1 peptide linked on the amino terminus to the foreign T helper site through a spacer is designated as SEQ ID NO: 6 (Table 1). Two experimental groups of three Duncan Hartley guinea pigs (female, 9 weeks old, 450 gm, virus-free) each were used in this immunogenicity study of PCV2 Cap1 vaccine formulations, as shown in Table 4.

resulted in more impressive anti-capsid titers for evidence of improved immunogenicity, as evaluated by either assay method (Table 4).

Immunogenicity Evaluation.

Immunogenicity testing of the designed PCV2 Cap1 peptide vaccine formulations was accomplished by target peptide-based ELISA using PCV2 peptide Cap1 (SEQ ID NO: 1) as solid phase antigen that had been coated on the wells at 2 μg/mL in 100 μL per well. Experimental animal sera serially diluted from 1:10 to 1:10,000 were tested and positive titers were expressed as $Log_{10}$ of the reciprocal dilution. Seropositive samples were pooled by group and immunogenicity results for the pools were determined by the Cap1 ELISA and by the IFA method (immunofluorescense assay). By this means, ELISA immunogenicities evaluated by reactivity to the Cap1 peptide were compared to the IFA titers evaluated by reactivity to full-length naturally configured PCV2 capsid protein expressed inside HTK cell line cells (FIGS. 1A and 1B).

Results

The results for group A show that the PCV2 Cap1 peptide (SEQ ID NO: 1) in the water-in-oil emulsion was immuno-

TABLE 4

Immunogenicity evaluation of Cap1 PCV2 vaccines in hosts by comparison of anti-capsid antibody titers determined by Cap1 peptide ELISA (Titer $Log_{10}$) and anti-capsid protein IFA

| Grp | Immunogen | Dose | Animal ID # | ELISA 0 wpi $A_{450}$ at 1/100 | ELISA 4 wpi Titer $Log_{10}$ | IFA titer 4 wpi |
|---|---|---|---|---|---|---|
| A | PCV2 Cap1 | Prime: 25 μg/0.25 ml/IM | 3963 | 0.050 | 4.108 | 100 |
| | (SEQ ID NO: 1) | Boost: 25 μg/0.25 ml/IM | 3964 | 0.055 | 3.280 | |
| | | (in ISA 50V2 1:1 v/v) | 3965 | 0.051 | 3.347 | |
| | | | Avg | 0.052 | 3.578 | |
| | | | SD | 0.002 | 0.376 | |
| B | UBITh3-KKK-εK- | Prime: 25 μg/0.25 ml/IM | 3957 | 0.053 | 4.349 | 400 |
| | PCV2 Cap1 | Boost: 25 μg/0.25 ml/IM | 3958 | 0.056 | 4.404 | |
| | (SEQ ID NO: 6) | (in ISA 50V2 1:1 v/v) | 3959 | 0.053 | 4.051 | |
| | | | Avg | 0.054 | 4.268 | |
| | | | SD | 0.001 | 0.155 | |

Each animal was immunized intramuscularly. For group A, peptide PCV2 Cap1 (SEQ ID NO: 1) was used as the immunogen which was formulated in a water-in-oil emulsion having Montanide™ ISA 50V2 (Seppic, Paris France), an oily adjuvant composition of mannide oleate and mineral oil commonly used for swine vaccines, emulsified with equal volumes of the aqueous phase peptide solution in PBS. For the vaccine given to group B, the Cap1 peptide was covalently linked at the amino terminus to the artificial combinatorial UBITh®3 T helper epitope (SEQ ID NO: 2) through a spacer of sequence Lys-Lys-Lys-ϵNLys (SEQ ID NO: 7) to bridge the targeted PCV Cap1 B cell epitopes and the UBITh®3 T cell epitope, resulting in the peptide immunogen designated as SEQ ID NO: 6 (Table 1), and formulated into the water-in-oil emulsion as was used for group A. Guinea pigs of groups A and B were administered 25 μg doses by the intramuscular route on weeks 0 (prime) and 2 (boost). The guinea pigs were bled on 0 and 4 weeks post-initial immunization (wpi) for immunogenicity testing of sera by both ELISA and IFA. As discussed below, a vaccine having the peptide immunogen without the covalently linked spacer and artificial UBITh®3 (SEQ ID No:1) elicited anti-Cap1 antibody responses; and, the use of the linked UBITh®3 T helper epitope, as in SEQ ID No: 6, genic on its own without linkage to the artificial Th epitope (SEQ ID NO: 2) at the 25 μg dose. Addition of the artificial combinatorial Th epitope through the multi-lysine spacer enhanced immunogenicity by an estimated five-fold (4.268-3.578=0.69 $Log_{10}$ in titer) as detected by ELISA. In a positive correlation with the Cap1-based ELISA results which serve to validate the Cap1 ELISA, the native capsid-based IFA method for determining immunogenicity for groups A and B also indicated an improved response to the artificial Th epitope-linked PCV2 peptide (SEQ ID NO: 6) over the Cap1 peptide by itself (SEQ ID NO: 1), although the less precise immunofluorescence assay indicated only a four-fold improvement, 100 vs. 400, for the chimerical SEQ ID NO: 6 immunogen. Similarly, piglets immunized with either the Cap1 peptide without (SEQ ID NO: 1) or with (SEQ ID NO: 6) linkage to the UBITh®3 T helper epitope (SEQ ID NO: 2) also display strong anti-Cap1 antibody responses with responses significantly improved by linkage to the SEQ ID NO: 2 T helper epitope (Example 5, Table 5).

The more immunogenic SEQ ID NO: 6 chimerical peptide was then tested in guinea pigs for its upper range of immunogenicity by administrations at a higher dosage with an additional adjuvant. A priming dose of 400 ng, in which the peptide immunogen was complexed with a CpG oligonucleotide adjuvant (SEQ ID No: 8) (27) in the amount described in Table 5, was injected followed by a booster dose of 100 μg of the CpG-augmented immunogen at 2 wpi. Immunogenicity exerted by this CpG-augmented higher dosage vaccination protocol yielded an unexpected ten-fold enhancement in immunogenicity by ELISA, and, consistent with that increase in ELISA titer, there was a 16-fold enhancement by IFA. That is, in comparison to the pooled group B IFA titer of 400 shown in Table 4, the guinea pig group immunized by the higher dosage CpG-augmented vaccine protocol reached an impressive IFA titer of 1600.

EXAMPLE 5

Immunogenicity Evaluation of PVC2 Cap1 Peptide Vaccine Formulations at Varying Doses in Piglets Raised on a Regular Farm Piglet Immunizations.

As shown in Table 5, 80 piglets at 4 weeks of age, on a regular not specific pathogen-free (SPF) farm, were divided into eight groups (ten piglets/group). These groups were immunized intramuscularly at weeks 0 and 4 with vaccines homogenized into Montanide™ ISA 50V2 as 1:1 (v/v) water-in-oil emulsions containing either 50 μg of peptide Cap1 (SEQ ID NO:1) and Tween® 80; or 50 to 400 μg of peptide Cap1 linked to the UBITh® 3 artificial Th epitope (SEQ ID NO: 6. The varying doses of the SEQ ID NO: 6 immunogen were complexed (27) or not complexed with the CpG oligonucleotide (SEQ ID NO: 7), before being formulated into the water-in-oil emulsions, in the presence or absence of Tween® 80 (Table 5).

Blood samples for ELISA analysis were collected at the time of first vaccination, and at 4 and 6 wpi. Individual sera were prepared and examined for PCV2 antibodies by ELISA as described in Examples 2 and 3. Sera from each group were pooled and subjected to further ELISA testing.

Results

Figure 2:
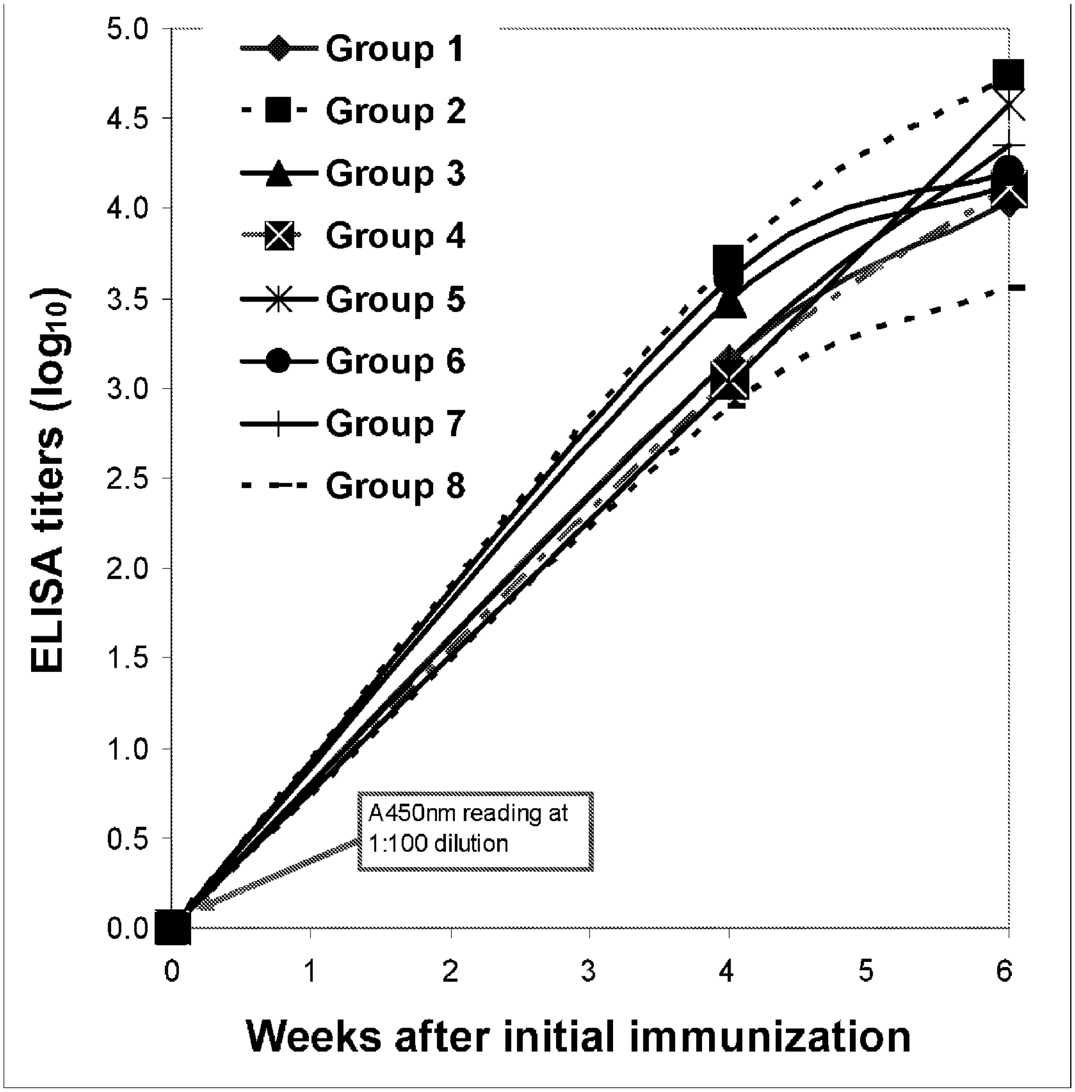
FIG. 2 is a graph that reports the immunogenicity of piglets raised on a regular farm with endemic PCV2 infection that were immunized with eight Cap1 peptide-based PCV2 vaccine formulations and doses as described in Table 5. Immunogenicity was evaluated by PCV2 Cap1 peptide-based ELISA (titer in $Log_{10}$).

Immunogenicity results by ELISA for the serum pools are shown by group in Table 5 and FIG. 2. All vaccine formulations were immunogenic even at the low 50 μg dose. Every piglet in each of the groups gave individual immune responses with ELISA titers of 1:1,000 or higher by weeks 4 and 6, and at over 1:10,000 by week 6 for the group pools, with the exception of the group 8 piglets that were given the unenhanced immunogen Cap1 peptide (SEQ ID NO: 1) at low 50 μg doses for both prime and boost.

TABLE 5

Immunogenicity evaluation of PCV2 Cap1 peptide vaccines. Vaccines varied by T helper epitope, peptide dose, and adjuvant formulation, administered to piglets raised on a regular farm, evaluation by Cap1 ELISA

| Grp No. # | Immunogen Description | Immunogen amount (μg/mL) | Additional Adjuvant§ | 0 wpi ($A_{450\ nm}$ at 1/100 dil) | ELISA titers ($Log_{10}$) 4 wpi | ELISA titers ($Log_{10}$) 6 wpi |
|---|---|---|---|---|---|---|
| 1 | UBITh ® 3-KKK-εK-Cap1* | Prime: 400 μg/1.0 mL<br>Boost: 100 μg/0.25 mL | CpG1 at 1.2:1‡ | 0.168 | 3.154 | 4.036 |
| 2 | UBITh ® 3-KKK-εK-Cap1* | Prime: 200 μg/2 mL<br>Boost: 200 μg/2 mL | 0.1% TWEEN ® 80 | 0.104 | 3.705 | 4.734 |
| 3 | UBITh ® 3-KKK-εK-Cap1* | Prime: 200 μg/2 mL<br>Boost: 200 μg/2 mL | none | 0.134 | 3.488 | 4.128 |
| 4 | UBITh ® 3-KKK-εK-Cap1* | Prime: 100 μg/1 mL<br>Boost: 100 μg/1 mL | CpG1 at 1.2:1‡<br>and<br>0.1% TWEEN ® 80 | 0.096 | 3.045 | 4.116 |
| 5 | UBITh ® 3-KKK-εK-Cap1* | Prime: 100μg/1 mL<br>Boost: 100μg/1 mL | 0.1% TWEEN ® 80 | 0.120 | 3.027 | 4.576 |
| 6 | UBITh ® 3-KKK-εK-Cap1* | Prime: 50 μg/0.5 mL<br>Boost: 50 μg/0.5 mL | 0.1% TWEEN ® 80 | 0.090 | 3.603 | 4.203 |
| 7 | UBITh ® 3-KKK-εK-Cap1* | Prime: 50 μg/0.5 mL<br>Boost: 50 μg/0.5 mL | none | 0.153 | 3.157 | 4.350 |
| 8 | Cap1† | Prime: 50 μg/0.5 mL<br>Boost: 50 μg/0.5 mL | 0.1% TWEEN ® 80 | 0.104 | 2.901 | 3.554 |

#Pooled sera used for each group

*SEQ ID NO: 6

†SEQ ID NO: 1

§All vaccines were 1:1 v/v water-in-oil emulsions with peptide dissolved in PBS or peptide/CpG complexes suspended in PBS as aqueous phase, Montanide ™ ISA 50V2 as oil phase and primary adjuvant, and indicated additional adjuvants.

‡Charge ratio of cationic peptide:anionic oligonucleotide.

Sera from individual pigs from weeks 0, 4, 6, and 10 were also evaluated for anti-capsid antibodies by IFA as described in Example 1. The IFA titers were found to be in the range of 400 to 1600 in most of the animals by week 10 with a few sera from group 3 having IFA titers as unexpectedly high as 6,400 after receiving two shots of the vaccine. No injection site reactogenicity was found in any of these pigs.

Among the 80 immunized piglets, eight were found to have maternally derived antibodies (MDA) as detected by IFA prior to the first immunization at week 0, as shown in Table 6. MDA are typically present in piglets raised on a regular farm in Taiwan and they typically act to inhibit anti-PCV capsid responses. In all eight piglets with MDA, anti-Cap1 antibodies of increasing titers were detected by ELISA between weeks 4 and 6 regardless of the doses and formulations given (Table 6). Thus, all eight animals with MDA had successful vaccine takes to the PCV2 Cap1 vaccine formulations despite interference by the presence of maternally-derived antibodies. This serves as evidence for the focused nature of the response to the vaccine of the invention.

IFA titers for immune sera collected 10 weeks after initial immunization from MDA-positive animals 26, 27, 86, and 87 had unprecedented IFA titers of 6400, 3200, 3200 and 3200, respectively. Comparable piglets having MDA were included for PCV2 vaccine studies with the Ft. Dodge/Wyeth (now Pfizer Animal Health) Suvaxyn® vaccine for PCV2, an inactivated virus vaccine, and with the Boehringer Ingleheim Inglevac® CircoFLEX® vaccine, a recombinant full length PCV2 ORF2 capsid protein vaccine. The piglets responded to those vaccines with IFA titers that did not develop beyond a usual range of 50-100, with only 5-10% reaching IFA titers up to 400. The "focused" nature of the responses to designed PCV2 Cap1 peptide immunogen thus differentiates the peptide-based vaccines from the already available types of PCV2 vaccines.

TABLE 6

Vaccine takes in piglets having maternally derived antibodies (MDA) prior to immunization by PCV2 Cap1 peptide-based vaccines at various doses.

| Individual Animal | IFA Titer* | Doses (μg per dose) | | Vaccine Take ELISA Titer ($Log_{10}$) | |
|---|---|---|---|---|---|
| Ear Tag No. | 0 wpi | Prime | Boost | 4 wpi | 6 wpi |
| 7 | 200 | 400 | 100 | 3.039 | 3.750 |
| 26 | 100 | 200 | 200 | 2.948 | 3.812 |
| 27 | 200 | 200 | 200 | 2.988 | 3.982 |
| 29 | 50 | 200 | 200 | 3.749 | 4.081 |
| 68 | 400 | 50 | 50 | 2.446 | 3.939 |
| 85 | 50 | 100 | 100 | 3.690 | 4.608 |
| 86 | 50 | 100 | 100 | 2.720 | 3.939 |
| 87 | 100 | 100 | 100 | 3.090 | 4.499 |

*MDA

Throughout the study period, the survival rate among the 80 pigs vaccinated with two shots of the various peptide Cap1 PCV2 vaccines was 93% while the survival rate for the 400 unvaccinated pigs housed in the same barn in this regular farm was 82%. The 93% survival rate for the vaccinees is a large improvement over the average survival rate of 80% for the 5000 pigs raised in the other housing facilities on this regular farm. This remarkable reduction in expected loss, an unintended result for this immunogenicity study, has further demonstrated the efficacy of Cap1 peptide-based PCV2 vaccines.

In summary, the Cap1 peptide PCV2 vaccines have shown significant immunogenicities from just a single dose as shown by ELISA titers at week 4, and have shown excellent immunogenicities by week 6 after two shots, with IFA titers reaching as high as 6400 in animals from group 3. All eight animals found to have prior maternally derived antibodies had immunogenic responses to the Cap1 vaccines regardless of the dose and formulation they received. The designed peptide-based PCV2 vaccines provided for a survival rate among vaccinated regular (non-SPF) piglets of 93% in comparison to the survival rate of 82% for the 400 unvaccinated piglets housed in the same building and in comparison to the 80% survival for another 5000 pigs housed in the other facilities of this regular farm, thus providing evidence for significant economic benefit.

EXAMPLE 6

Cap1 Peptide PCV2 Vaccine Improved for One Shot Protection by Addition to the Formulation of Clustered T Helper Cell Peptides from the ORF1 and ORF3 Proteins of PCV2

Immunogenicity of the Cap1 peptide PCV2 vaccine was further improved by incorporating the PCV2 T cell epitope peptides encoded by ORF 1 and ORF 3 and shown in Table 1. These epitopes were initially tested by Stevenson et al (12) for their induction of T cell proliferation in swine. PCV2 Cap1 peptide (for example SEQ ID NOS: 1 or 6) mixed with an equimolar combination of the three short PCV2 Th peptides (SEQ ID NOS.: 3, 4 and 5) at molar ratios from 1:1 down to 1:0.1 to 1:0.05 were formulated in the water phase prior to emulsion preparation. A PCV2 Cap1 vaccine formulation supplemented by these immunodominant PCV2 Th epitopes was tested on piglets to determine the effect on the immune response through the stimulation of PCV2-related T cell responses, including cytokine production, after a single shot of the vaccine.

Results

As shown in Table 7, significantly enhanced IFA titers were observed in piglets given a lower dose PCV2 Cap1 vaccine formulation with the supplemental PCV2 Th peptides. IFA titers of 50 to 400 were developed by week 4 in the group 10 piglets given a single dose of vaccine having 50 μg of Cap1 peptide immunogen with linked UBITh®3 (SEQ ID NO: 6) mixed with 20 μg of the three PCV2 T helper peptide immunogens (SEQ ID NOS: 3, 4, 5), in comparison to the IFA titers of <50 to 50 seen in the group 9 piglets at week 4 who received a single dose of a vaccine having 200 μg of the SEQ ID NO: 6 Cap1 immunogen without the three additional PCV2 Th peptide immunogens.

Therefore, a vaccine formulation containing a predominantly B cell epitope-clustered PCV2 capsid peptide (SEQ ID NO: 6) in combination with the equimolar mixture of immunodominant Th peptides from other PCV2 proteins (SEQ ID NOS.: 3, 4 and 5) provided for immunogen sparing by allowing for a lower total dose of immunogen content while maintaining balanced B cell antibody responses and T cell responses, and thereby exerting effective protective immune responses against infection with lower doses of peptide immunogen. Significant immunogen-sparing results by the three supplemental PCV Th peptides were also obtained when a Cap1 immunogen without linked UBITh®3 (SEQ ID NO: 1) was the target B cell immunogenic peptide in comparable vaccine formulations with and without the supplemental Th immunogens (Table 8). In this outcome, the dose having 50 μg of SEQ ID NO: 1 with 10 μg of the supplemental Th peptides was more effective than 100 and 200 μg doses of SEQ ID NO: 1 without the three supplemental Th peptides. Such combination Cap1 vaccine formulations should be particularly effective when supplied as an inexpensive low dose one shot vaccine intended for emergency use.

TABLE 7

Induction of IFA antibody titers against PCV2 capsid after single immunization of piglets with Cap1 peptide vaccines without or with PCV2 ORF1 and ORF3 Th epitope peptides

| Grp No. | Vaccine Formulation | Animal ID | IFA Titer 0 wpi | 2 wpi | 4 wpi |
|---|---|---|---|---|---|
| 9 | 200 μg SEQ ID NO: 6 in 2 mL (1:1 v/v emulsion with ISA 50V2) | 154-03 | <50 | <50 | <50 |
| | | 154-07 | <50 | 50 | 50 |
| | | 152-03 | <50 | <50 | <50 |
| | | 152-10 | <50 | <50 | <50 |
| | | 152-04 | <50 | <50 | <50 |
| 10 | 50 μg SEQ ID NO: 6 + 20 μg SEQ ID NOS: 3, 4 and 5 at equal weights in 1 mL (1:1 v/v emulsion with ISA 50V2) | 139-01 | <50 | <50 | 200 |
| | | 139-02 | <50 | <50 | 50 |
| | | 139-05 | <50 | <50 | 200 |
| | | 139-13 | <50 | <50 | 200 |
| | | 139-15 | <50 | <50 | 200 |
| | | 139-03 | <50 | <50 | 400 |
| | | 139-04 | <50 | 50 | 200 |
| | | 139-10 | <50 | <50 | 400 |
| | | 139-12 | <50 | <50 | 200 |
| | | 139-14 | <50 | <50 | 400 |

EXAMPLE 7

Cap1 Peptide PCV2 Vaccine Tested for Ability to Provide Protection to Piglets from Virus Transmission and Pathogenicity Caused by Exposure to PCV2-Infected Pigs A field trial was designed to evaluate the ability of Cap1 peptide PCV2 vaccines to elicit protective immunity in a variety of doses and formulations. SPF (specific pathogen-free) piglets that were exposed to PCV2 by being housed together with otherwise pathogen-free piglets carrying PCV2 infection were vaccinated with Cap1 vaccines. These conditions, designed for testing the vulnerability of specially housed transgenic pigs to infection by the natural transmission of PCV2, are ideally suited for assessing the protective immunity provided by a PCV2 vaccine.

Housing Conditions for PCV2-Infected and Germ-Free Animals

The facility used for the field trial is the "Transgenic Animal Testing Station" (TATS) at Xiang Hill Ranch in northern Taiwan. TATS is used for the safety testing of transgenic pigs being kept under quarantine prior to intentional release to the field. It is managed by the Department of Animal Medicine of the Animal Technology Institute of Taiwan (ATIT) (23). The laboratories, animal housing, and animal management practices are in compliance with the guidelines of ISO/IEC 17025:2005 and ISO9001 (SGS TW07/03565). The transgenic pigs of the farm are routinely monitored for SPF status by observation and routine tests for Classical Swine Fever, pseudorabies virus, porcine reproductive and respiratory syndrome virus, hog cholera virus, atrophic rhinitis, *Mycoplasma hyopneumoniae*, foot-and-mouth disease virus, Swine Dysentery, Scabies, *toxoplasma* and *Actinobacillus pleuropneumoniae*. Routine monitoring found no evidence for the presence of these infectious diseases and agents.

In addition, testing for PCV2 infection by the recently developed IFA test described in Example 1 has been used for the past two years, and this pig population was found to have widespread PCV2 infection. The PCV2 positive rate of this farm, as determined by serological surveillance, has reached as high as 89.4% (47/52). These otherwise SPF animals have PCV2 as the only circulating pathogen.

Conditions for PCV2 Vaccination and Exposure

The selection of germ-free piglets from this "PCV2 only" environment began by identifying expectant sows that were negative for PCV2 antibodies first in serum and later in colostrum, by PCV2 IFA titer. Piglets from sows with serum and colostrum both negative were enrolled in the trial at about four weeks of age. At this time, the germ-free piglets were randomly divided into five groups, five piglets per group for vaccine groups 11-13, 15 piglets for vaccine group 14, and six piglets for control group 15. The vaccine groups were then administered the PCV2 Cap1 vaccine priming doses described in Table 8 (100 or 200 mg of SEQ ID NO: 1, or either 50 μg of SEQ ID NO: 1+50 μg of SEQ ID NOS: 3, 4, and 5 in equal weights or 50 mg of SEQ ID NO: 1+10 μg of SEQ ID NOS: 3, 4, and 5 in equal weights) by intramuscular injection (i.m.). At 4 weeks post-initial immunization (wpi), the groups were given booster doses of the same vaccines. Antibody responses were monitored by IFA at 2, 6, and 10 wpi. The IFA titers, seen in Table 8, were at baseline level for all groups at 2 wpi. High antibody responses were achieved for all vaccinated groups by week 6 although immunogenicity varied for the groups at 6 and 10 wpi. Titers for the control group remained at baseline throughout the period of serological testing.

The germ-free piglets, in both the vaccinated and control groups, were housed together in a barn with the general population of "PCV2 only" transgenic pigs for about two months, putting them at risk for transmission of PCV2. At the end of this period, when the weights of all the experimental pigs had reached approximately 120 kg liveweight (at 5-6 months age), the animals were sacrificed and examined for evidence of PCV2 infection by necropsy.

Figure 3A:
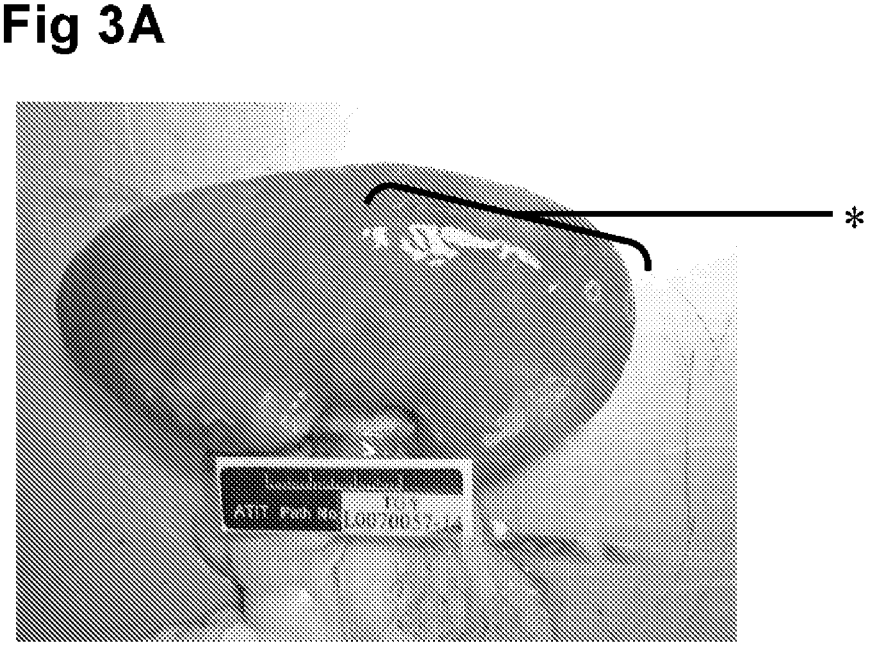
FIG. 3A is a photograph of a kidney of an unvaccinated pig infected by PCV2. Lesions are bracketed (*).
Figure 3B:
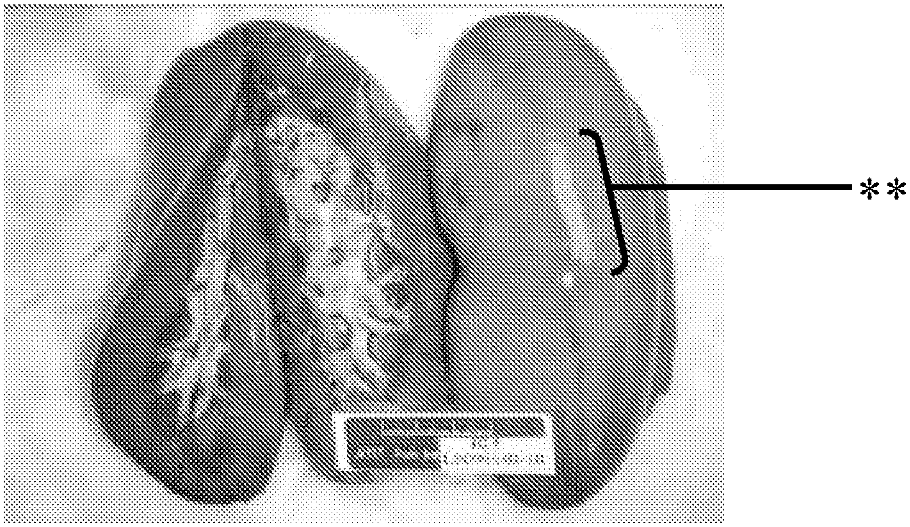
FIG. 3B is a photograph of the kidneys from an uninfected vaccinated pig, one sectioned (left), one intact (right). Light reflection from the flash is bracketed (**).

Signs of PCV2 infection were subtle and many pathological lesions that appeared during PCV2 infection were not found after recovery during the two month exposure period. Therefore, a necropsy procedure, one that provides for more sensitive diagnosis than the usual more direct methods used to examine the vaccinated animals of a vaccine/challenge study or field trial for signs of infection by the transmitted pathogen, was used as the method for detecting infection in the vaccinated/exposed animals. Necropsy examinations included observations of lymph nodes, lung and kidney. Little evidence for infection was found except for signs of lesions on the kidneys of control animals. White spots and streaks were retained as signs of fibrosis on the surfaces of kidneys of unvaccinated, infected animals, as shown in FIG. 3A (*), while such signs marking a history of lesions were absent from the kidneys of vaccinated pigs scored as having no lesions as shown in FIG. 3B (the dull white streak seen in FIG. 3B is reflected light (**)).

The pathology results scored from the necropsies on the experimental pigs, shown in Table 9, were obtained with white spots on the kidney capsule being the predominant indication of prior infection. This trial was conducted with PCV2 peptide vaccine formulations under code.

Results and Conclusions

The results of PCV2 antibody titers by PCV 2 IFA for both of control and vaccine testing groups, Table 8, show increasing antibody responses over time in the vaccinated animals with higher responses by 10 wpi. The immunogenicities of the Cap1 peptide-based PCV2 vaccine formulations varied and the most immunogenic was the formulation given to the largest group, group 14.

Three out of six pigs in the control group (50%) were found to have white spots on the kidney capsule as the typical lesions marking a history of PCV2 infection (FIG. 3A), with one of the control pigs having slight lesions and two having moderate lesions. In contrast, only two out of 30 vaccinated pigs (6.7%) displayed pathological changes, and these were both scored for having slight evidence of kidney pathology (Table 9). These two were found only among the largest group of vaccinated pigs, group 14 with 15 pigs. No pathological changes at all were noted for lymph nodes and lungs in the vaccinated pigs, with only slight kidney lesions noted for two of the vaccinees. Thus, protective efficacy is demonstrated for multiple formulations and doses of the peptide-based PCV2 vaccine of this disclosure.

In the specification, the inventors have not attempted to exhaustively enumerate all possible variations. That alternate embodiments may not have been presented for a specific portion of the invention, and may result from a different combination of described portions, or that other undescribed alternate embodiments may be available for a portion, is not to be considered a disclaimer of those alternate embodiments. It will be appreciated that many of those undescribed embodiments are within the literal scope of the following claims, and others are equivalent. Furthermore, all references, publications, U.S. patents, and U.S. patent application Publications cited throughout this specification are hereby incorporated by reference as if fully set forth in this specification.

TABLE 8

Geometric mean antibody titers by IFA for each group of pigs after immunizations with Cap1 peptide vaccines with or without PCV2 ORF1 and ORF2 T epitope peptides

| Grp No. | Vaccine Description*† | No. of Animals | IFA Titer 2 wpi | 6 wpi | 10 wpi |
|---|---|---|---|---|---|
| 11 | SEQ ID NO: 1 200 μg/2 mL | 5 | 10 | 48 | 66 |
| 12 | SEQ ID NO: 1 100 μg/1 mL | 5 | 10 | 60 | 105 |
| 13 | 50 μg SEQ ID No: 1 + 50 μg SEQ ID NOS: 3, 4, 5 in equal ratio/1 mL | 5 | 10 | 100 | 100 |
| 14 | 50 μg SEQ ID No: 1 + 10 μg SEQ ID NOS: 3, 4, 5 in equal ratio/1 mL | 15 | 10 | 127 | 174 |
| 15 | Control | 6 | 10 | 10 | 10 |

*All formulations were 1:1 v/v water-in-oil emulsions with Montanide™ ISA 50V2 as adjuvant.
†Vaccine given i.m. in two shots with priming dose given at 0 wpi and booster dose at 4 wpi.

TABLE 9

Observations of PCV2 pathology in the experimental pigs

| Grp No. | Vaccine Description* | No. of Animals | Animal No. | Score† |
|---|---|---|---|---|
| 11 | SEQ ID NO: 1 (200 μg/2 mL) | 5 | 154-03 | 0 |
| | | | 154-07 | 0 |
| | | | 152-03 | 0 |
| | | | 152-10 | 0 |
| | | | 152-04 | 0 |
| 12 | SEQ ID NO: 1 (100 μg/1 mL) | 5 | 135-01 | 0 |
| | | | 135-02 | 0 |
| | | | 135-03 | 0 |
| | | | 135-10 | 0 |
| | | | 135-14 | 0 |
| 13 | 50 μg SEQ ID No: 1 + 50 μg SEQ ID NOS: 3, 4, 5 in equal ratio/1 mL | 5 | 135-04 | 0 |
| | | | 135-11 | 0 |
| | | | 135-12 | 0 |
| | | | 135-13 | 0 |
| | | | 135-15 | 0 |
| 14 | 50 μg SEQ ID No: 1 + 10 μg SEQ ID NOS: 3, 4, 5 in equal ratio/1 mL | 15 | 141-04 | 0 |
| | | | 140-11 | 0 |
| | | | 140-01 | 0 |
| | | | 140-02 | 1 |
| | | | 140-10 | 0 |
| | | | 140-12 | 0 |
| | | | 141-01 | 0 |
| | | | 141-05 | 0 |
| | | | 140-14 | 0 |
| | | | 140-03 | 0 |
| | | | 154-02 | 0 |
| | | | 154-06 | 0 |
| | | | 154-05 | 0 |
| | | | 152-02 | 0 |
| | | | 152-01 | 1 |
| 1-4 total | | 30 | 2/30 = 6.7% infected | |
| 15 | Control | 6 | 140-04 | 0 |
| | | | 139-11 | 2 |
| | | | 146-03 | 2 |
| | | | 146-11 | 1 |
| | | | 146-12 | 0 |
| | | | 146-10 | 0 |
| 5 total | | 6 | 3/6 = 50% infected | |

*Same two dose vaccinations as described in Table 8.
†Score: 0 = no lesions, 1 = slight, 2 = moderate, 3 = severe

The invention claimed is:

1. A porcine circovirus type 2 (PCV2) vaccine composition, comprising a peptide antigen and a veterinarily acceptable delivery vehicle or adjuvant, wherein the peptide antigen consists essentially of:
   - a) an amino acid sequence of about 154 residues having at least 85% sequence identity to SEQ ID NO: 1;
   - b) an artificial combinatorial T helper epitope; and
   - c) an optional heterologous spacer, wherein the amino acid sequence of (a) is covalently linked to the artificial combinatorial T helper epitope of (b) directly or through the optional heterologous spacer of (c).

2. The PCV2 vaccine according to claim 1, wherein the amino acid sequence of (a) is SEQ ID NO: 1.

3. The PCV2 vaccine according to claim 1, wherein the amino acid sequence of (a) is selected from the group consisting of SEQ ID NOs:
   9-19 and 20.

4. The PCV2 vaccine according to claim 1, wherein the charge of the peptide antigen is altered by adding or deleting 1 to 5 amino acids.

5. The PCV2 vaccine according to claim 1, wherein the artificial combinatorial T helper epitope of (b) is covalently linked to the amino terminus of the amino acid sequence of (a).

6. The PCV2 vaccine according to claim 5, wherein the artificial combinatorial T helper epitope of (b) is covalently linked to the amino terminus of the amino acid sequence of (a) through the optional heterologous spacer of (c), wherein the optional heterologous spacer comprises at least one amino acid.

7. The PCV2 vaccine according to claim 5, wherein the artificial combinatorial T helper epitope of (b) is SEQ ID NO:2.

8. The PCV2 vaccine according to claim 6, wherein the optional heterologous spacer of (c) is SEQ ID NO:7.

9. The PCV2 vaccine according to claim 1, further comprising an equimolar mixture of three PCV2 T helper epitope peptides of SEQ ID NOS: 3, 4, and 5.

10. The PCV2 vaccine according to claim 9, wherein the total amount of the equimolar mixture of SEQ ID NOS: 3, 4, and 5 is between about 1 µg to about 100 µg.

11. The PCV2 vaccine according to claim 1, wherein the total amount of the peptide antigen is between about 10 µg to about 1 mg.

12. The PCV2 vaccine according to claim 1, wherein the delivery vehicle or adjuvant is selected from the group consisting of an oily adjuvant composition of mannide oleate and mineral oil for production of water-in-oil emulsions, Polyoxyethylene (20) sorbitan monooleate, and a CpG oligonucleotide.

13. The PCV2 vaccine according to claim 1, where in the peptide antigen is SEQ ID NO: 6.

14. The PCV2 vaccine according to claim 1, wherein the amino acid sequence of (a) has at least 90% sequence identity to SEQ ID NO: 1.

15. The PCV2 vaccine according to claim 1, wherein the amino acid sequence of (a) has at least 95% sequence identity to SEQ ID NO: 1.

16. The PCV2 vaccine according to claim 1, wherein the artificial combinatorial T helper epitope of (b) is SEQ ID NO: 2.

17. A porcine circovirus type 2 (PCV2) vaccine composition comprising:
   - a) a peptide antigen selected from the group consisting of:
     - i) a B cell epitope cluster peptide of about 154 residues corresponding to about amino acid position 47 to about amino acid position 202 of a full-length PCV2 capsid protein; and
     - ii) the B cell epitope cluster peptide in (i) covalently linked to an artificial combinatorial T helper epitope directly or through an optional heterologous spacer;
   - b) a mixture of three PCV2 T helper epitope peptides of SEQ ID NOS: 3, 4, and 5; and
   - c) a veterinarily acceptable delivery vehicle or adjuvant.

18. A PCV2 vaccine composition, comprising a peptide antigen of SEQ ID NO: 6 and a veterinarily acceptable delivery vehicle or adjuvant, wherein the amount of peptide antigen is between about 10 µg to about 1 mg.

19. A method for protecting piglets that are or are not PCV2 MDA positive against PCV2 infection, comprising administering a porcine circovirus type 2 (PCV2) vaccine composition comprising a peptide antigen and a veterinarily acceptable delivery vehicle or adjuvant, wherein the peptide antigen is selected from the group consisting of:
   - a) an amino acid sequence of about 154 residues having at least 85% sequence identity to SEQ ID NO: 1: and
   - b) the amino acid sequence of (a) covalently linked to an artificial combinatorial T helper epitope directly or through an optional heterologous spacer.

20. A method for diagnosing PCV2 infection comprising the steps of
   - a) attaching a peptide antigen to a solid support, wherein the peptide antigen is an amino acid sequence of about 154 residues having at least 85% sequence identity to SEQ ID NO: 1:
   - b) exposing said peptide antigen attached to said solid support to a swine blood, serum or plasma sample under conditions conducive to binding of an antibody to the peptide antigen, and
   - c) detecting the presence of antibodies bound to said peptide antigen attached to said solid support.

* * * * *

SEQUENCE LISTING

```
<160> NUMBER OF SEQ ID NOS: 20

<210> SEQ ID NO 1
<211> LENGTH: 154
<212> TYPE: PRT
<213> ORGANISM: Porcine circovirus
<220> FEATURE:
<221> NAME/KEY: MISC_FEATURE
<222> LOCATION: (1)..(154)
<223> OTHER INFORMATION: Type 2 strain Cyc08 from Taiwan

<400> SEQUENCE: 1

Thr Arg Leu Ser Arg Thr Phe Gly Tyr Thr Val Lys Ala Thr Thr Val
1               5                   10                  15

Arg Thr Pro Ser Trp Ala Val Asp Met Met Arg Phe Asn Ile Ser Asp
            20                  25                  30
```

-continued

```
Phe Val Pro Pro Gly Gly Gly Thr Asn Lys Ile Ser Ile Pro Phe Glu
        35                  40                  45

Tyr Tyr Arg Ile Arg Lys Val Lys Val Glu Phe Trp Pro Cys Ser Pro
    50                  55                  60

Ile Thr Gln Gly Asp Arg Gly Val Gly Ser Thr Ala Val Ile Leu Asp
65                  70                  75                  80

Asp Asn Phe Val Thr Lys Ala Thr Ala Leu Thr Tyr Asp Pro Tyr Val
                85                  90                  95

Asn Tyr Ser Ser Arg His Thr Ile Pro Gln Pro Phe Ser Tyr His Ser
            100                 105                 110

Arg Tyr Phe Thr Pro Lys Pro Val Leu Asp Ser Thr Ile Asp Tyr Phe
        115                 120                 125

Gln Pro Asn Asn Lys Arg Asn Gln Leu Trp Leu Arg Leu Gln Thr Ser
    130                 135                 140

Ala Asn Val Asp His Val Gly Leu Gly Thr
145                 150
```

<210> SEQ ID NO 2
<211> LENGTH: 19
<212> TYPE: PRT
<213> ORGANISM: Measles virus
<220> FEATURE:
<221> NAME/KEY: MISC_FEATURE
<222> LOCATION: (1)..(19)
<223> OTHER INFORMATION: Modified T helper site
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R

<400> SEQUENCE: 2

```
Ile Ser Ile Xaa Glu Ile Xaa Xaa Val Ile Val Xaa Xaa Ile Glu Thr
1               5                   10                  15

Ile Leu Phe
```

<210> SEQ ID NO 3
<211> LENGTH: 20
<212> TYPE: PRT
<213> ORGANISM: Porcine circovirus
<220> FEATURE:
<221> NAME/KEY: MISC_FEATURE
<222> LOCATION: (1)..(20)
<223> OTHER INFORMATION: T helper epitope 1 from PCV2 ORF1

<400> SEQUENCE: 3

```
Cys His Ile Glu Lys Ala Lys Gly Thr Asp Gln Gln Asn Lys Glu Tyr
1               5                   10                  15

Cys Ser Lys Glu
            20
```

<210> SEQ ID NO 4
<211> LENGTH: 20
<212> TYPE: PRT
<213> ORGANISM: Porcine circovirus
<220> FEATURE:
<221> NAME/KEY: MISC_FEATURE
<222> LOCATION: (1)..(20)
<223> OTHER INFORMATION: T helper epitope 2 from PCV2 ORF1

<400> SEQUENCE: 4

```
Lys Trp Trp Asp Gly Tyr His Gly Glu Glu Val Val Val Ile Asp Asp
1               5                   10                  15

Phe Tyr Gly Trp
            20
```

<210> SEQ ID NO 5
<211> LENGTH: 20
<212> TYPE: PRT
<213> ORGANISM: Porcine circovirus
<220> FEATURE:
<221> NAME/KEY: MISC_FEATURE
<222> LOCATION: (1)..(20)
<223> OTHER INFORMATION: T helper epitope 1 from PCV2 ORF3

<400> SEQUENCE: 5

```
Pro Arg Trp Pro His Asn Asp Val Tyr Ile Gly Leu Pro Ile Thr Leu
1               5                   10                  15

Leu His Phe Pro
            20
```

<210> SEQ ID NO 6
<211> LENGTH: 177
<212> TYPE: PRT
<213> ORGANISM: Artificial Sequence
<220> FEATURE:
<223> OTHER INFORMATION: B cell epitope cluster peptide derived from PCV2 ORF2 capsid protein (Cap1 peptide) linked through spacer to artificial combinatorial Th peptide (UBITh3)
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: MOD_RES
<222> LOCATION: (23)..(23)
<223> OTHER INFORMATION: AMIDATION, (epsilonN)Lys

<400> SEQUENCE: 6

```
Ile Ser Ile Xaa Glu Ile Xaa Xaa Val Ile Val Xaa Xaa Ile Glu Thr
1               5                   10                  15

Ile Leu Phe Lys Lys Lys Lys Thr Arg Leu Ser Arg Thr Phe Gly Tyr
            20                  25                  30
```

-continued

```
Thr Val Lys Ala Thr Thr Val Arg Thr Pro Ser Trp Ala Val Asp Met
        35                  40                  45

Met Arg Phe Asn Ile Ser Asp Phe Val Pro Pro Gly Gly Gly Thr Asn
    50                  55                  60

Lys Ile Ser Ile Pro Phe Glu Tyr Tyr Arg Ile Arg Lys Val Lys Val
65                  70                  75                  80

Glu Phe Trp Pro Cys Ser Pro Ile Thr Gln Gly Asp Arg Gly Val Gly
                85                  90                  95

Ser Thr Ala Val Ile Leu Asp Asp Asn Phe Val Thr Lys Ala Thr Ala
            100                 105                 110

Leu Thr Tyr Asp Pro Tyr Val Asn Tyr Ser Ser Arg His Thr Ile Pro
        115                 120                 125

Gln Pro Phe Ser Tyr His Ser Arg Tyr Phe Thr Pro Lys Pro Val Leu
    130                 135                 140

Asp Ser Thr Ile Asp Tyr Phe Gln Pro Asn Asn Lys Arg Asn Gln Leu
145                 150                 155                 160

Trp Leu Arg Leu Gln Thr Ser Ala Asn Val Asp His Val Gly Leu Gly
                165                 170                 175

Thr


<210> SEQ ID NO 7
<211> LENGTH: 4
<212> TYPE: PRT
<213> ORGANISM: artificial
<220> FEATURE:
<223> OTHER INFORMATION: artificial spacer sequence
<220> FEATURE:
<221> NAME/KEY: MOD_RES
<222> LOCATION: (4)..(4)
<223> OTHER INFORMATION: AMIDATION, (epsilonN)Lys

<400> SEQUENCE: 7

Lys Lys Lys Lys
1


<210> SEQ ID NO 8
<211> LENGTH: 24
<212> TYPE: DNA
<213> ORGANISM: Artificial Sequence
<220> FEATURE:
<223> OTHER INFORMATION: CpG oligo nucleotide

<400> SEQUENCE: 8

tcgtcgtttt gtcgttttgt cgtt                                              24


<210> SEQ ID NO 9
<211> LENGTH: 154
<212> TYPE: PRT
<213> ORGANISM: Porcine circovirus
<300> PUBLICATION INFORMATION:
<308> DATABASE ACCESSION NUMBER: GenBank/ACC59783
<309> DATABASE ENTRY DATE: 2008-04-21
<313> RELEVANT RESIDUES IN SEQ ID NO: (1)..(154)

<400> SEQUENCE: 9

Thr Arg Leu Ser Arg Thr Phe Gly Tyr Thr Ile Lys Arg Thr Thr Val
1               5                   10                  15

Arg Thr Pro Ser Trp Ala Val Asp Met Met Arg Phe Asn Ile Asn Asp
            20                  25                  30

Phe Leu Pro Pro Gly Gly Gly Ser Asn Pro Arg Ser Val Pro Phe Glu
        35                  40                  45
```

-continued

```
Tyr Tyr Arg Ile Arg Lys Val Lys Val Glu Phe Trp Pro Cys Ser Pro
    50                  55                  60

Ile Thr Gln Gly Asp Arg Gly Val Gly Ser Ser Ala Val Ile Leu Asp
65                  70                  75                  80

Asp Asn Phe Val Thr Lys Ala Thr Ala Leu Thr Tyr Asp Pro Tyr Val
                85                  90                  95

Asn Tyr Ser Ser Arg His Thr Ile Thr Gln Pro Phe Ser Tyr His Ser
            100                 105                 110

Arg Tyr Phe Thr Pro Lys Pro Val Leu Asp Ser Thr Ile Asp Tyr Phe
        115                 120                 125

Gln Pro Asn Asn Lys Arg Asn Gln Leu Trp Leu Arg Leu Gln Thr Ala
    130                 135                 140

Gly Asn Val Asp His Val Gly Leu Gly Thr
145                 150


<210> SEQ ID NO 10
<211> LENGTH: 154
<212> TYPE: PRT
<213> ORGANISM: Porcine circovirus
<300> PUBLICATION INFORMATION:
<308> DATABASE ACCESSION NUMBER: GenBank/ACQ99546
<309> DATABASE ENTRY DATE: 2010-06-28
<313> RELEVANT RESIDUES IN SEQ ID NO: (1)..(154)

<400> SEQUENCE: 10

Thr Arg Leu Ser Arg Thr Phe Gly Tyr Thr Ile Lys Arg Thr Thr Val
1               5                   10                  15

Lys Thr Pro Ser Trp Ala Val Asp Met Met Arg Phe Asn Ile Asn Asp
            20                  25                  30

Phe Leu Pro Pro Gly Gly Gly Ser Asn Pro Arg Ser Val Pro Phe Glu
        35                  40                  45

Tyr Tyr Arg Ile Arg Lys Val Lys Val Glu Phe Trp Pro Cys Ser Pro
    50                  55                  60

Ile Thr Gln Gly Asp Arg Gly Val Gly Ser Ser Ala Val Ile Leu Asp
65                  70                  75                  80

Asp Asn Phe Val Thr Lys Ala Thr Ala Leu Thr Tyr Asp Pro Tyr Val
                85                  90                  95

Asn Tyr Ser Ser Arg His Thr Ile Thr Gln Pro Phe Ser Tyr His Ser
            100                 105                 110

Arg Tyr Phe Thr Pro Lys Pro Val Leu Asp Ser Thr Ile Asp Tyr Phe
        115                 120                 125

Gln Pro Asn Asn Lys Arg Asn Gln Leu Trp Leu Arg Leu Gln Thr Ala
    130                 135                 140

Gly Asn Val Asp His Val Gly Leu Gly Thr
145                 150


<210> SEQ ID NO 11
<211> LENGTH: 154
<212> TYPE: PRT
<213> ORGANISM: Porcine circovirus
<300> PUBLICATION INFORMATION:
<308> DATABASE ACCESSION NUMBER: GenBank/ACX47360
<309> DATABASE ENTRY DATE: 2010-02-03
<313> RELEVANT RESIDUES IN SEQ ID NO: (1)..(154)

<400> SEQUENCE: 11

Thr Arg Leu Ser Arg Thr Phe Gly Tyr Thr Ile Lys Arg Thr Thr Val
1               5                   10                  15

Lys Thr Pro Ser Trp Ala Val Asp Met Met Arg Phe Asn Ile Asn Asp
```

20 25 30

Phe Leu Pro Pro Gly Gly Gly Ser Asn Pro Arg Ser Val Pro Phe Glu
35 40 45

Tyr Tyr Arg Ile Arg Lys Val Lys Val Glu Phe Trp Pro Cys Ser Pro
50 55 60

Ile Thr Gln Gly Asp Arg Gly Val Gly Ser Ser Ala Val Ile Leu Asp
65 70 75 80

Asp Asn Phe Val Thr Lys Ala Thr Ala Leu Thr Tyr Asp Pro Tyr Val
85 90 95

Asn Tyr Ser Ser Arg His Thr Ile Thr Gln Pro Phe Ser Tyr His Ser
100 105 110

Arg Tyr Phe Thr Pro Lys Pro Val Leu Asp Ser Thr Ile Asp Tyr Phe
115 120 125

Gln Pro Asn Asn Lys Arg Asn Gln Leu Trp Met Arg Leu Gln Thr Ser
130 135 140

Arg Asn Val Asp His Val Gly Leu Gly Thr
145 150

<210> SEQ ID NO 12
<211> LENGTH: 150
<212> TYPE: PRT
<213> ORGANISM: Porcine circovirus
<300> PUBLICATION INFORMATION:
<308> DATABASE ACCESSION NUMBER: GenBank/ACV53396
<309> DATABASE ENTRY DATE: 2010-03-17
<313> RELEVANT RESIDUES IN SEQ ID NO: (1)..(150)

<400> SEQUENCE: 12

Arg Thr Phe Gly Tyr Thr Val Lys Arg Thr Pro Val Arg Thr Pro Ser
1 5 10 15

Trp Ala Val Asp Met Met Arg Phe Asn Ile Asn Asp Phe Leu Pro Pro
20 25 30

Gly Gly Gly Ser Asn His Arg Ser Val Pro Phe Glu Tyr Tyr Arg Ile
35 40 45

Arg Lys Val Lys Val Glu Phe Trp Pro Cys Ser Pro Ile Thr Gln Gly
50 55 60

Asp Arg Gly Val Gly Ser Ser Ala Val Ile Leu Asp Asp Asn Phe Val
65 70 75 80

Thr Lys Ala Thr Ala Leu Thr Tyr Asp Pro Tyr Val Asn Tyr Ser Ser
85 90 95

Arg His Thr Ile Thr Gln Pro Phe Ser Tyr His Ser Arg Tyr Phe Thr
100 105 110

Pro Lys Pro Val Leu Asp Ser Thr Ile Asp Tyr Phe Gln Pro Asn Asn
115 120 125

Lys Arg Asn Gln Leu Trp Leu Arg Leu Gln Thr Ala Gly Asn Val Asp
130 135 140

His Val Gly Leu Gly Thr
145 150

<210> SEQ ID NO 13
<211> LENGTH: 154
<212> TYPE: PRT
<213> ORGANISM: Porcine circovirus
<300> PUBLICATION INFORMATION:
<308> DATABASE ACCESSION NUMBER: GenBank/ADI44325
<309> DATABASE ENTRY DATE: 2010-06-14
<313> RELEVANT RESIDUES IN SEQ ID NO: (1)..(154)

<400> SEQUENCE: 13

```
Thr Arg Leu Ser Arg Thr Ile Gly Tyr Thr Val Lys Lys Thr Thr Val
1               5                   10                  15

Arg Thr Pro Ser Trp Asn Val Asp Met Met Arg Phe Asn Ile Asn Asp
            20                  25                  30

Phe Leu Pro Pro Gly Gly Gly Ser Asn Pro Leu Thr Val Pro Phe Glu
        35                  40                  45

Tyr Tyr Arg Ile Arg Lys Val Lys Val Glu Phe Trp Pro Cys Ser Pro
    50                  55                  60

Ile Thr Gln Gly Asp Arg Gly Val Gly Ser Thr Ala Val Ile Leu Asp
65                  70                  75                  80

Asp Asn Phe Val Thr Lys Ala Asn Ala Leu Thr Tyr Asp Pro Tyr Val
                85                  90                  95

Asn Tyr Ser Ser Arg His Thr Ile Thr Gln Pro Phe Ser Tyr His Ser
            100                 105                 110

Arg Tyr Phe Thr Pro Lys Pro Val Leu Asp Arg Thr Ile Asp Tyr Phe
        115                 120                 125

Gln Pro Asn Asn Lys Arg Asn Gln Leu Trp Leu Arg Leu Gln Thr Thr
    130                 135                 140

Gly Asn Val Asp His Val Gly Leu Gly Thr
145                 150


<210> SEQ ID NO 14
<211> LENGTH: 154
<212> TYPE: PRT
<213> ORGANISM: Porcine circovirus
<300> PUBLICATION INFORMATION:
<308> DATABASE ACCESSION NUMBER: GenBank/ADD25772
<309> DATABASE ENTRY DATE: 2010-03-08
<313> RELEVANT RESIDUES IN SEQ ID NO: (1)..(154)

<400> SEQUENCE: 14

Thr Arg Leu Ser Arg Thr Ile Gly Tyr Thr Val Lys Lys Thr Thr Val
1               5                   10                  15

Arg Thr Pro Ser Trp Asn Val Asp Met Met Arg Phe Asn Ile Asn Asp
            20                  25                  30

Phe Leu Pro Pro Gly Gly Gly Ser Asn Pro Leu Thr Met Pro Phe Glu
        35                  40                  45

Tyr Tyr Arg Ile Arg Lys Val Lys Val Glu Phe Trp Pro Cys Ser Pro
    50                  55                  60

Ile Thr Gln Gly Asp Arg Gly Val Gly Ser Thr Ala Val Ile Leu Asp
65                  70                  75                  80

Asp Asn Phe Val Thr Lys Ala Asn Ala Leu Thr Tyr Asp Pro Tyr Val
                85                  90                  95

Asn Tyr Ser Ser Arg His Thr Ile Thr Gln Pro Phe Ser Tyr His Ser
            100                 105                 110

Arg Tyr Phe Thr Pro Lys Pro Val Leu Asp Arg Thr Ile Asp Tyr Phe
        115                 120                 125

Gln Pro Asn Asn Lys Arg Asn Gln Leu Trp Leu Arg Leu Gln Thr Thr
    130                 135                 140

Gly Asn Val Asp His Val Gly Leu Gly Thr
145                 150


<210> SEQ ID NO 15
<211> LENGTH: 154
<212> TYPE: PRT
<213> ORGANISM: Porcine circovirus
<300> PUBLICATION INFORMATION:
```

<308> DATABASE ACCESSION NUMBER: GenBank/ADB97547
<309> DATABASE ENTRY DATE: 2010-08-18
<313> RELEVANT RESIDUES IN SEQ ID NO: (1)..(154)

<400> SEQUENCE: 15

```
Ala Arg Leu Ser Arg Thr Phe Gly Tyr Thr Val Lys Arg Thr Thr Val
1               5                   10                  15

Thr Thr Pro Ser Trp Ala Val Asp Met Met Arg Phe Lys Leu Asp Asp
            20                  25                  30

Phe Val Pro Pro Gly Gly Gly Thr Asn Lys Ile Ser Ile Pro Phe Glu
        35                  40                  45

Tyr Tyr Arg Ile Arg Lys Val Lys Val Glu Phe Trp Pro Cys Ser Pro
    50                  55                  60

Ile Thr Gln Gly Asp Arg Gly Val Gly Ser Thr Ala Val Ile Leu Asp
65                  70                  75                  80

Asp Asn Phe Val Pro Lys Ala Asn Ala Leu Thr Tyr Asp Pro Tyr Val
                85                  90                  95

Asn Tyr Ser Phe Arg His Thr Ile Pro Gln Pro Phe Ser Tyr His Ser
            100                 105                 110

Arg Tyr Phe Thr Pro Lys Pro Val Leu Asp Ser Thr Ile Asp Tyr Phe
        115                 120                 125

Gln Pro Asn Asn Lys Arg Asn Gln Leu Trp Met Arg Ile Gln Thr Ser
    130                 135                 140

Arg Asn Val Asp His Val Gly Leu Gly Thr
145                 150
```

<210> SEQ ID NO 16
<211> LENGTH: 154
<212> TYPE: PRT
<213> ORGANISM: Porcine circovirus
<300> PUBLICATION INFORMATION:
<308> DATABASE ACCESSION NUMBER: GenBank/ABW76695
<309> DATABASE ENTRY DATE: 2008-08-01
<313> RELEVANT RESIDUES IN SEQ ID NO: (1)..(154)

<400> SEQUENCE: 16

```
Thr Arg Leu Ser Arg Thr Phe Gly Tyr Thr Val Lys Arg Thr Thr Val
1               5                   10                  15

Thr Thr Pro Ser Trp Ala Val Asp Met Met Arg Phe Lys Leu Asp Asp
            20                  25                  30

Phe Val Pro Pro Gly Gly Gly Thr Asn Lys Ile Ser Ile Pro Phe Glu
        35                  40                  45

Tyr Tyr Arg Ile Arg Lys Val Lys Val Glu Phe Trp Pro Cys Ser Pro
    50                  55                  60

Ile Thr Gln Gly Asp Arg Gly Val Gly Ser Thr Ala Val Ile Leu Asp
65                  70                  75                  80

Asp Asn Phe Val Pro Lys Ala Asn Ala Leu Thr Tyr Asp Pro Tyr Val
                85                  90                  95

Asn Tyr Ser Ser Arg His Thr Ile Pro Gln Pro Phe Ser Tyr His Ser
            100                 105                 110

Arg Tyr Phe Thr Pro Lys Pro Val Leu Asp Ser Thr Ile Asp Tyr Phe
        115                 120                 125

Gln Pro Asn Asn Lys Lys Asn Gln Leu Trp Leu Arg Leu Gln Thr Ser
    130                 135                 140

Arg Asn Val Asp His Val Gly Leu Gly Thr
145                 150
```

```
<210> SEQ ID NO 17
<211> LENGTH: 154
<212> TYPE: PRT
<213> ORGANISM: Porcine circovirus
<300> PUBLICATION INFORMATION:
<308> DATABASE ACCESSION NUMBER: GenBank/ABI29888
<309> DATABASE ENTRY DATE: 2007-06-14
<313> RELEVANT RESIDUES IN SEQ ID NO: (1)..(154)

<400> SEQUENCE: 17

Ala Arg Leu Ser Arg Thr Phe Gly Tyr Thr Val Lys Ala Thr Thr Val
1               5                   10                  15

Ser Thr Pro Ser Trp Ala Val Asp Met Met Arg Phe Asn Leu Asp Asp
            20                  25                  30

Phe Val Pro Pro Gly Gly Gly Thr Asn Lys Ile Ser Ile Pro Phe Glu
        35                  40                  45

Tyr Tyr Arg Ile Arg Lys Val Lys Val Glu Phe Trp Pro Cys Ser Pro
    50                  55                  60

Ile Thr Gln Gly Asp Arg Gly Val Gly Ser Ser Ala Ile Ile Leu Asp
65                  70                  75                  80

Asp Asn Phe Val Ile Lys Ala Thr Ala Gln Thr Tyr Asp Pro Tyr Val
                85                  90                  95

Asn Tyr Ser Ser Arg His Thr Ile Pro Gln Pro Phe Ser Tyr His Ser
            100                 105                 110

Arg Tyr Phe Thr Pro Lys Pro Val Leu Asp Ser Thr Ile Asp Tyr Phe
        115                 120                 125

Gln Pro Asn Asn Lys Arg Asn Gln Leu Trp Met Arg Leu Gln Thr Ser
    130                 135                 140

Arg Asn Val Asp His Val Gly Leu Gly Thr
145                 150


<210> SEQ ID NO 18
<211> LENGTH: 154
<212> TYPE: PRT
<213> ORGANISM: Porcine circovirus
<300> PUBLICATION INFORMATION:
<308> DATABASE ACCESSION NUMBER: GenBank/YP_003422531
<309> DATABASE ENTRY DATE: 2010-06-28
<313> RELEVANT RESIDUES IN SEQ ID NO: (1)..(154)

<400> SEQUENCE: 18

Thr Arg Leu Ser Arg Thr Phe Gly Tyr Thr Val Lys Ala Thr Thr Val
1               5                   10                  15

Arg Thr Pro Ser Trp Ala Val Asp Met Met Arg Phe Asn Ile Asp Asp
            20                  25                  30

Phe Val Pro Pro Gly Gly Gly Thr Asn Lys Ile Ser Ile Pro Phe Glu
        35                  40                  45

Tyr Tyr Arg Ile Arg Lys Val Lys Val Glu Phe Trp Pro Cys Ser Pro
    50                  55                  60

Ile Thr Gln Gly Asp Arg Gly Val Gly Ser Thr Ala Val Ile Leu Asp
65                  70                  75                  80

Asp Asn Phe Val Thr Lys Ala Thr Ala Leu Thr Tyr Asp Pro Tyr Val
                85                  90                  95

Asn Tyr Ser Ser Arg His Thr Ile Pro Gln Pro Phe Ser Tyr His Ser
            100                 105                 110

Arg Tyr Phe Thr Pro Lys Pro Val Leu Asp Ser Thr Ile Asp Tyr Phe
        115                 120                 125

Gln Pro Asn Asn Lys Arg Asn Gln Leu Trp Met Arg Leu Gln Thr Ser
    130                 135                 140
```

Arg Asn Val Asp His Val Gly Leu Gly Thr
145 150

<210> SEQ ID NO 19
<211> LENGTH: 154
<212> TYPE: PRT
<213> ORGANISM: Porcine circovirus
<300> PUBLICATION INFORMATION:
<308> DATABASE ACCESSION NUMBER: GenBank/AAN62766
<309> DATABASE ENTRY DATE: 2002-11-06
<313> RELEVANT RESIDUES IN SEQ ID NO: (1)..(154)

<400> SEQUENCE: 19

Thr Arg Leu Ser Arg Thr Phe Gly Tyr Thr Val Lys Ala Thr Thr Val
1 5 10 15

Arg Thr Pro Ser Trp Ala Val Asp Met Met Arg Phe Asn Ile Asn Asp
20 25 30

Phe Val Pro Pro Gly Gly Gly Thr Asn Lys Ile Ser Ile Pro Phe Glu
35 40 45

Tyr Tyr Arg Ile Arg Lys Val Lys Val Glu Phe Trp Pro Cys Ser Pro
50 55 60

Ile Thr Gln Gly Asp Arg Gly Val Gly Ser Thr Ala Val Ile Leu Asp
65 70 75 80

Asp Asn Phe Val Thr Lys Ala Thr Ala Leu Thr Tyr Asp Pro Tyr Val
85 90 95

Asn Tyr Ser Ser Arg His Thr Ile Pro Gln Pro Phe Ser Tyr His Ser
100 105 110

Arg Tyr Phe Thr Pro Lys Pro Val Leu Asp Ser Thr Ile Asp Tyr Phe
115 120 125

Gln Pro Asn Asn Lys Arg Asn Gln Leu Trp Leu Arg Leu Gln Thr Ser
130 135 140

Ala Asn Val Asp His Val Gly Leu Gly Thr
145 150

<210> SEQ ID NO 20
<211> LENGTH: 154
<212> TYPE: PRT
<213> ORGANISM: Artificial Sequence
<220> FEATURE:
<223> OTHER INFORMATION: Porcine circovirus - consensus sequence

<400> SEQUENCE: 20

Thr Arg Leu Ser Arg Thr Phe Gly Tyr Thr Val Lys Arg Thr Pro Val
1 5 10 15

Arg Thr Pro Ser Trp Ala Val Asp Met Met Arg Phe Asn Ile Asn Asp
20 25 30

Phe Leu Pro Pro Gly Gly Gly Ser Asn His Arg Ser Ile Pro Phe Glu
35 40 45

Tyr Tyr Arg Ile Arg Lys Val Lys Val Glu Phe Trp Pro Cys Ser Pro
50 55 60

Ile Thr Gln Gly Asp Arg Gly Val Gly Ser Thr Ala Val Ile Leu Asp
65 70 75 80

Asp Asn Phe Val Thr Lys Ala Thr Ala Leu Thr Tyr Asp Pro Tyr Val
85 90 95

Asn Tyr Ser Ser Arg His Thr Ile Thr Gln Pro Phe Ser Tyr His Ser
100 105 110

Arg Tyr Phe Thr Pro Lys Pro Val Leu Asp Ser Thr Ile Asp Tyr Phe
115 120 125

-continued

```
Gln Pro Asn Asn Lys Arg Asn Gln Leu Trp Leu Arg Leu Gln Thr Ser
    130                 135                 140

Ala Asn Val Asp His Val Gly Leu Gly Thr
145                 150
```